United States Patent
Le et al.

(10) Patent No.: US 10,344,043 B2
(45) Date of Patent: Jul. 9, 2019

(54) ANTIVIRAL AND ANTIBACTERIA AGENTS BASED ON QUATERNARY AMMONIUM COMPOUND COMPLEXED WITH BORIC ACID AND ITS DERIVATIVES

(71) Applicant: B-Organic Films Corp

(72) Inventors: Tien Canh Le, Montreal (CA); Giuliano Lafrenière Di Fruscia, Mont-Royal (CA)

( * ) Notice: Subject to any disclaimer, the term of this patent is extended or adjusted under 35 U.S.C. 154(b) by 0 days.

(21) Appl. No.: 15/566,766

(22) PCT Filed: Apr. 14, 2016

(86) PCT No.: PCT/CA2016/050431
§ 371 (c)(1),
(2) Date: Oct. 16, 2017

(87) PCT Pub. No.: WO2016/165019
PCT Pub. Date: Oct. 20, 2016

(65) Prior Publication Data
US 2018/0127439 A1   May 10, 2018

Related U.S. Application Data

(60) Provisional application No. 62/147,161, filed on Apr. 14, 2015.

(51) Int. Cl.
| | |
|---|---|
| *C07F 5/04* | (2006.01) |
| *C07F 5/05* | (2006.01) |
| *A23L 33/00* | (2016.01) |
| *A23L 17/40* | (2016.01) |
| *A23L 33/16* | (2016.01) |
| *A61P 31/12* | (2006.01) |
| *A61P 31/20* | (2006.01) |
| *A61P 31/14* | (2006.01) |
| *A61P 31/04* | (2006.01) |
| *C07F 5/02* | (2006.01) |

(52) U.S. Cl.
CPC ............... *C07F 5/04* (2013.01); *A23L 17/40* (2016.08); *A23L 33/16* (2016.08); *A23L 33/30* (2016.08); *A61P 31/04* (2018.01); *A61P 31/12* (2018.01); *A61P 31/14* (2018.01); *A61P 31/20* (2018.01); *C07F 5/025* (2013.01); *C07F 5/05* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 1,788,680 | A | * 1/1931 | Ludecke | ............... C07C 213/08 564/8 |
| 2008/0236663 | A1 | 10/2008 | Tanabe et al. | |

FOREIGN PATENT DOCUMENTS

| | | | |
|---|---|---|---|
| DE | 479016 A1 | 7/1929 | |
| WO | 2010130708 | 11/2010 | |
| WO | WO-2010130708 A1 * | 11/2010 | ............. A61K 31/69 |
| WO | 2013123456 | 8/2013 | |
| WO | 2014107535 | 7/2014 | |
| WO | WO-2014107535 A1 * | 7/2014 | ........... A61K 31/407 |

OTHER PUBLICATIONS

ISR of PCT/CA2016/050431, Jun. 15, 2016.
Supplementary European Search Report of corresponding EP application 16779368.6, dated Nov. 29, 2018.
Lee et al: "Betaine:Homocysteine Methyltransferase from Rat Liver: Purification and Inhibition by a Boronic Acid Substrate Analog", Archives of Biochemistry and Biophysics, Jan. 1992, pp. 77-86.
Bickelhaupt et al.: "Preparation and some properties of trimethylaminemethylenetriphenylborane", Recueil des travaux chimiques des Pays-Bas, Jan. 1968, pp. 188-192.

* cited by examiner

*Primary Examiner* — Heidi Reese
(74) *Attorney, Agent, or Firm* — Benoit & Cote, Inc.; Mathieu Miron

(57) ABSTRACT

The present document describes compounds resulting from the complexation of quaternary ammonium compounds with boric acid and/or its derivatives, and methods of making the same, and methods of using the same for the treatment of pathogenic infections.

8 Claims, 16 Drawing Sheets
Specification includes a Sequence Listing.

SEQUENCE LISTING

<160> NUMBER OF SEQ ID NOS: 24

<210> SEQ ID NO 1
<211> LENGTH: 23
<212> TYPE: DNA
<213> ORGANISM: Vibrio parahaemolyticus

<400> SEQUENCE: 1 ggaagttta acccgtaacg agc        23

<210> SEQ ID NO 2
<211> LENGTH: 24
<212> TYPE: DNA
<213> ORGANISM: Vibrio parahaemolyticus

<400> SEQUENCE: 2
ggtacaaatg agttgatagc ctcg        24

<210> SEQ ID NO 3
<211> LENGTH: 20
<212> TYPE: DNA
<213> ORGANISM: white spot syndrome baculovirus

<400> SEQUENCE: 3
gctggtgggg gatgatacta        20

<210> SEQ ID NO 4
<211> LENGTH: 20
<212> TYPE: DNA
<213> ORGANISM: white spot syndrome baculovirus

<400> SEQUENCE: 4
gtctcccgtc accgtcttta        20

<210> SEQ ID NO 5
<211> LENGTH: 24
<212> TYPE: DNA
<213> ORGANISM: Unknown
<220> FEATURE:
<223> OTHER INFORMATION: Litopenaeus vannamei

<400> SEQUENCE: 5
gggcttcatt aacaacctaa ttgc        24

<210> SEQ ID NO 6
<211> LENGTH: 22
<212> TYPE: DNA
<213> ORGANISM: Unknown
<220> FEATURE:
<223> OTHER INFORMATION: Litopenaeus vannamei

<400> SEQUENCE: 6
atgttggtcc agaagatggt gt        22

<210> SEQ ID NO 7
<211> LENGTH: 20
<212> TYPE: DNA
<213> ORGANISM: Unknown
<220> FEATURE:
<223> OTHER INFORMATION: Litopenaeus vannamei

<400> SEQUENCE: 7
taggcaatgt catccccatt         20

<210> SEQ ID NO 8
<211> LENGTH: 21
<212> TYPE: DNA
<213> ORGANISM: Unknown
<220> FEATURE:
<223> OTHER INFORMATION: Litopenaeus vannamei

<400> SEQUENCE: 8
tcctgaagga agctttacac g        21

<210> SEQ ID NO 9
<211> LENGTH: 20
<212> TYPE: DNA
<213> ORGANISM: Unknown
<220> FEATURE:
<223> OTHER INFORMATION: Litopenaeus vannamei

<400> SEQUENCE: 9
caagcgaacc tctggaaatc         20

<210> SEQ ID NO 10
<211> LENGTH: 19
<212> TYPE: DNA
<213> ORGANISM: Unknown
<220> FEATURE:
<223> OTHER INFORMATION: Litopenaeus vannamei

<400> SEQUENCE: 10
tggcaaatcc aggtagagc          19

<210> SEQ ID NO 11
<211> LENGTH: 19
<212> TYPE: DNA
<213> ORGANISM: Unknown
<220> FEATURE:
<223> OTHER INFORMATION: Litopenaeus vannamei

<400> SEQUENCE: 11
gccctaaatg atggatgac          19

<210> SEQ ID NO 12
<211> LENGTH: 18
<212> TYPE: DNA
<213> ORGANISM: Unknown
<220> FEATURE:
<223> OTHER INFORMATION: Litopenaeus vannamei

<400> SEQUENCE: 12
gccaagggaa aaagaaat           18

<210> SEQ ID NO 13
<211> LENGTH: 18
<212> TYPE: DNA
<213> ORGANISM: Unknown
<220> FEATURE:
<223> OTHER INFORMATION: Litopenaeus vannamei

<400> SEQUENCE: 13
ccacactgct cacattgc                                                  18

<210> SEQ ID NO 14
<211> LENGTH: 18
<212> TYPE: DNA
<213> ORGANISM: Unknown
<220> FEATURE:
<223> OTHER INFORMATION: Litopenaeus vannamei

<400> SEQUENCE: 14
gaaggtctcc acgcacat                                                  18

<210> SEQ ID NO 15
<211> LENGTH: 18
<212> TYPE: DNA
<213> ORGANISM: Unknown
<220> FEATURE:
<223> OTHER INFORMATION: Litopenaeus vannamei

<400> SEQUENCE: 15
tgggacgaca tggagaag                                                  18

<210> SEQ ID NO 16
<211> LENGTH: 18
<212> TYPE: DNA
<213> ORGANISM: Unknown
<220> FEATURE:
<223> OTHER INFORMATION: Litopenaeus vannamei

<400> SEQUENCE: 16
gggggtgttg aaggtctc                                                  18

<210> SEQ ID NO 17
<211> LENGTH: 24
<212> TYPE: DNA
<213> ORGANISM: Unknown
<220> FEATURE:
<223> OTHER INFORMATION: Litopenaeus vannamei

<400> SEQUENCE: 17
ccgtctccta taaactcgtc actc                                           24

<210> SEQ ID NO 18
<211> LENGTH: 21
<212> TYPE: DNA
<213> ORGANISM: Unknown
<220> FEATURE:
<223> OTHER INFORMATION: Litopenaeus vannamei

<400> SEQUENCE: 18
tcgccgtagt tttcaatgtt c                                              21

<210> SEQ ID NO 19
<211> LENGTH: 18
<212> TYPE: DNA
<213> ORGANISM: Unknown
<220> FEATURE:
<223> OTHER INFORMATION: Litopenaeus vannamei

<400> SEQUENCE: 19
tcgtcggagg aactgacg                                                  18

<210> SEQ ID NO 20
<211> LENGTH: 18

```
<212> TYPE: DNA
<213> ORGANISM: Unknown
<220> FEATURE:
<223> OTHER INFORMATION: Litopenaeus vannamei

<400> SEQUENCE: 20
tgccctcatc cacatcct                                              18

<210> SEQ ID NO 21
<211> LENGTH: 18
<212> TYPE: DNA
<213> ORGANISM: Unknown
<220> FEATURE:
<223> OTHER INFORMATION: Litopenaeus vannamei

<400> SEQUENCE: 21
tcctggctca cacacctg                                              18

<210> SEQ ID NO 22
<211> LENGTH: 18
<212> TYPE: DNA
<213> ORGANISM: Unknown
<220> FEATURE:
<223> OTHER INFORMATION: Litopenaeus vannamei

<400> SEQUENCE: 22
gtccttcagc gagccttg                                              18

<210> SEQ ID NO 23
<211> LENGTH: 20
<212> TYPE: DNA
<213> ORGANISM: Unknown
<220> FEATURE:
<223> OTHER INFORMATION: Litopenaeus vannamei

<400> SEQUENCE: 23
cgtccttcca gttctaccat                                            20

<210> SEQ ID NO 24
<211> LENGTH: 20
<212> TYPE: DNA
<213> ORGANISM: Unknown
<220> FEATURE:
<223> OTHER INFORMATION: Litopenaeus vannamei

<400> SEQUENCE: 24
atctggatgt agcccttgtt                                            20
```

ANTIVIRAL AND ANTIBACTERIA AGENTS BASED ON QUATERNARY AMMONIUM COMPOUND COMPLEXED WITH BORIC ACID AND ITS DERIVATIVES

CROSS-REFERENCE TO RELATED APPLICATIONS

This application is a US National Phase under 35 USC § 371 of PCT/CA2016/050431, filed Apr. 14, 2016, which claims priority from and the benefit of U.S. Provisional Patent Application 62/147,161 filed Apr. 14, 2015, the specification of which is hereby incorporated by reference in its entirety.

BACKGROUND

(A) Field

The subject matter disclosed generally relates to compounds resulting from the complexation of quaternary ammonium compounds with boric acid and/or its derivatives, and methods of making the same.

(b) Related Prior Art

In recent years, the shrimp aquaculture industry is rapidly expanded and according to the Food and Agriculture Organization of the United Nations (FAO), approximately 3.5 million metric tons (corresponding to an estimated value $15 billion) by year were produced. Despite the economic importance, the global shrimp farming industry continues to be plagued by various diseases which stand out as serious impediments in its progress. It is estimated that about of 60% of losses in shrimp aquaculture have been caused by viral pathogens and 20% by bacterial pathogens (Flegel, T. W., Lightner, D. V., Lo, C. F., Owens, L. 2008. In: «Diseases in Asian Aquaculture VI». Bondad-Reantaso, M. G., Mohan, C. V., Crumlish, M. and Subasinghe, R. P. Eds. Fish Health Section», Asian Fisheries Society, Manila, Philippines, p. 355-378).

Depending on the species of shrimp involved, the clinical manifestations are different for each diseases, for example pathogens such as Taura Syndrome Virus (TSV) cause cuticular melanized spots, Yellow head Virus (YHV) for yellowing of the cephalothorax and bleaching of the body, particularly White Spot Syndrome Virus (WSSV), as mentioned its name, induced white spots on the inside surface of the carapace, appendages and cuticle. It is of interest to mention that WSSV is the most serious and devastating pathogen of farmed shrimp worldwide because it is highly lethal and contagious, killing shrimp quickly. Outbreaks of WSSV disease have wiped out within a few days the entire populations of many shrimp farms throughout the world. Spreading from Taiwan to Asia, then to Central, South and North America (Zuidema, D., Van Hulten, M. C. W., Marks, H., Witteveldt, J., Vlak, J. M. 2004. In: Current trends in the study of bacterial and viral fish and shrimp diseases. Leung, K. Y. Ed.), World Scientific, Singapore, p. 237-255), the shrimp WSSV is currently the only member of both the *Whispovirus* genus and the Nimaviridae family which can infect more than 90 species of aquatic crustaceans.

In addition to infections caused by virus, many pathogenic bacteria can also cause serious problems to the farming industries. The most important is due to *Vibrio* responsible to vibriosis. Generally, these bacteria are considered to be opportunistic pathogens causing disease when shrimp are stressed. Although the exoskeleton provides an effective physical barrier to certain pathogens, *Vibrio* spp. are among the chitinoclastic bacteria associated with shell disease and may enter through wounds in the exoskeleton or pores of crustaceans. Vibriosis is a common problem world-wide, not only responsible for chronic mortalities of crustaceans, but also serious problems for shellfish, flatfish and finfish cultures. It is worth mentioning that problems caused by vibriosis are common, but are considered minor compared to viral epidemics.

White Spot Syndrome Virus (WSSV)

In 1993, WSSV was first described as white spot disease outbreaks in prawn *Penaeus japonicus* farmed in Japan. Around the same time, similar disease and mortalities in other prawn species was observed in Taiwan and China, from where it is suspected to have originated. The virus was known under various names which are mainly related to *baculovirus* such as «Chinese *baculovirus*», «Systemic ectodermal and mesodermal *baculovirus*» and «White spot *baculovirus*», etc. Currently, based on its unique morphological and genetic features similarities, the viruses were grouped collectively into the white spot virus complex with WSSV being adopted as the generic virus name. WSSV are now considered by the International Committee on Taxonomy of Viruses to represent a new virus genus, called «*Whispovirus*», within the family Nimaviridae.

Morphology and Ultrastructure of WSSV

To date, the morphology and ultrastructure of WSSV is not yet fully understood. However, it has been observed that the WSSV virions show an ovoid particle morphology with average size about of 300 nm in length and 120 nm in diameter. The viral envelope has the structure of an apparently lipidic bilayer membrane surrounded the nucleocapsid that it is tightly packed within the virion.

The WSSV viral envelope consists of at least 35 different proteins, of which VP28 and VP26 are the most abundant, accounting for approximately 60% of the envelope. VP28, encoded by open reading frame (ORF) 421 (wsv421), is the major envelope protein and several studies suggest that VP28 may play a crucial role in the initial steps of systemic WSSV infection in shrimp, particularly as an attachment protein, binding the virus to shrimp cells, and helping it to enter into the cytoplasm.

With regard to VP26, the product encoded by wsv311 gene, was first identified as being associated to the nucleocapsid. It is likely that the VP26 is capable of binding to actin or actin-associated proteins. After internalization into the host cell, viruses must be transported near the site of transcription and replication, where its genome is delivered. Thus, it has been suggested that as a major component of the viral nucleocapsid, VP26 may help WSSV to move toward the nucleus by interacting with actin or cellular actin-binding proteins.

The viral genome is a double-stranded circular DNA molecule and the full length sequence was submitted to GenBank (Accession number: AF440570). Generally, the genome of WSSV estimated approximately to be 300 kbp and contains 292967 nucleotides encompassing 184 major ORF. However, only 6% of the WSSV ORFs could be demonstrated a putative function involved in nucleotide metabolism, DNA replication, and protein modification (Van Hulten, M. C., Witteveldt, J., Peters, S., Kloosterboer, N., Tarchini, R., Fiers, M., Sandbrink, H., Lankhorst, R. K., Vlak, J. M. 2001. 286, 7-22).

Strategies for the Control of WSSV

Due to the impact that WSSV has caused to shrimp cultures all over the world, several approaches have been used for the management of the disease. However, it is worth noting that at present there is no treatment available to interfere with the unrestrained occurrence and spread of the disease.

Shrimp Anti-WSSV Immune Response

In mammals, active immunity has been practiced for the control of viral infection symptoms. Active immunity is resulting by the self-immune capacity stimulated the production of antibodies against pathogens which are administered under inactivated or attenuated forms into species such as humans or animal.

In contrast, invertebrates such as crustaceans lack a true adaptive immune system and no specific immune function uses antibodies to recognize and destroy non-self material. For this reason, the passive immunity is also envisaged and the processes is generated by administering pathogens to domestic animals such as birds to obtain the corresponding antibodies, which are then used for the control of shrimp infection symptoms. However, the in vivo defense mechanism of invertebrates is significantly different from the immune mechanism of vertebrates, and there has been no concrete disclosure about the effectiveness of passive immunity for the control of infection symptoms of invertebrates such as shrimp.

It is suggested that hemocytes plays an important part in the defense system employed by crustaceans against pathogens, since they initiate coagulation, delay WSSV infection and inhibiting viral replication. However, the precise mechanism of action of hemocyanin is not clear.

Regardless the active or passive immunity, these processes are only specific for one type of pathogen. In this case, it is preferable to use a product with a larger spectrum of action to effectively control at the same time different pathogens (bacteria and virus).

Treatment of Infected Animals

Even though there are several methods and products developed recently to attempt to control these pathogens, none have been successful and the research for new effective products seems urgent and necessary. Until now, no commercial reagents with proven abilities to clear completely WSSV infections or for prophylaxis in the event of outbreaks of WSD exist. Similar observation can be made for other virus such as Taura Syndrome Virus or Yellow head Virus.

Vibrio parahaemolyticus

Many pathogenic bacteria can also cause serious problems to the farming industries. The most important is due to Vibrio (gram-negative bacteria in the family Vibrionaceae) responsible to vibriosis. This disease has been reported in penaeid shrimp culture including at least 14 species: *Vibrio harveyi, V. splendidus, V. parahaemolyticus, V. alginolyticus, V. anguillarum, V. vulnificus, V. campbelli, V. fischeri, V. damsella, V. pelagicus, V. orientalis, V. ordalii, V. mediterrani, V. logei*, etc.

As a control measure antibiotics are generally used against bacterial infection symptoms including *vibrio* disease. Recently, due to a large dissemination of antibiotics, the appearance of resistant bacteria has become problematic, and in addition, the administration of antibiotics does not guarantee a sufficient control effect. Also, there has not been any efficacious medicine developed for viral infection symptoms, and accordingly, it can be said that there is no effective control measure.

Other Pathogens

There are numerous pathogens responsible for aquatic animal diseases, and they stem from various etiologies such as viruses, bacteria, fungi or parasites. It is worth noting that all these pathogens constitute serious problems for aquaculture farming including:

1. Taura Syndrome Virus (TSV) is an emerging disease, caused by a virus in the family Dicistroviridae, genus *cripavirus* that affects Pacific white shrimp in their post-larval, juvenile and sub-adult life stages. The mortality rate for these life stages can reach up to 90%;
2. Yellow Head Virus (YHV) is another emerging disease that affects Giant Tiger shrimp (*Penaeus monodon*), especially in the early and late juvenile life stages, which is highly lethal and contagious, killing shrimp quickly. YHV belongs to the family Roniviridae;
3. Other virus such as Infectious Hypodermal and Haematopoietic Necrosis (IHHNV), Spherical *Baculovirus*, Spawner-isolated Mortality Virus Disease, Spring Viremia of Carp (SVC caused by Rhabdoviruses), Koi Herpes Virus (KHV), Large Mouth Bass Virus (LMBV), *Baculovirus penaei* (BP), etc, are also problematic.

Human Pathogens

There numerous bacteria such as: i) Enterobacteriacae (i.e. *Escheria coli, Salmonella, Shigella*, etc.); ii) *Clostridium botulinum*; iii) *Listeria monocytogenes*, etc. and viral such as Herpesviridae, Retroviridae, Filoviridae (Ebola virus), etc. responsible for serious, even fatal, illness in human.

Though several products have been developed to prevent and treat pathogens in, such as genetic vaccines, these have proven ineffective in commercial operations, impractical to apply for lack of effective delivery mechanisms, or expensive.

Therefore, there is a need for novel antipathogenic agents and compositions comprising the same.

Also, there is a need for novel composition for the treatment or prevention of pathogenic infections.

SUMMARY

In the present invention, the use of boric acid and its derivatives, in a complex with a quaternary ammonium compound, preferably choline chloride (due to its natural origin such as from phosphatidylcholine), form a quaternary complex able to control infections caused by many bacteria and virus for human and animal, particularly for use in aquatic animal farming industries.

According to an embodiment, there is provided a compound of formula I, or a pharmaceutically acceptable salts thereof, and stereoisomers thereof:

wherein $R^1$, $R^2$, $R^3$, and $R^4$ are independently selected from alkyl, cycloalkyl, or aryl, optionally substituted with at one or more —OH, and each of said $R^1$, $R^2$, $R^3$, and $R^4$ may be optionally connected to another of said $R^1$, $R^2$, $R^3$, and $R^4$;

$R^5$ is selected from —$BO_2$, —$BO_3$, —$BO_4$, —$B_2O_3$, —$B_2O_4$, —$B_3O_5$, —$B_3O_7$, —$B_4O_7$, —$B_4O_9$—$B_5O_8$, —O—$BR^6R^7$;

$R^6$ is selected from —H, —OH, alkyl, alkenyl, aryl, —O—$R^8$;
$R^7$ is absent or selected from —H, —OH, alkyl, alkenyl, aryl, and —O—$R^8$;
$R^8$ is selected from —H, alkyl, alkenyl, aryl.

The $R^1$ may be $CH_2$—$CH_2$.

The $R^2$, $R^3$, and $R^4$ may be independently $CH_3$, $CH_2$—$CH_3$, or $CH_2$—$CH_2$—$CH_3$.

The $R^1$ may be $CH_2$—$CH_2$, $R^2$, $R^3$, and $R^4$ may be independently $CH_3$.

The $R^5$ may be —$B_5O_8$.

The $R^5$ may be —O—$BR^6R^7$.

The $R^5$ may be —O—$B(OH)_2$.

The compound may be selected from the following compounds:

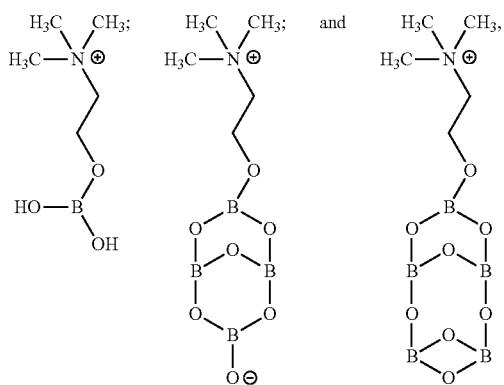

or a combination thereof.

The compound may be a combination of the following compounds:

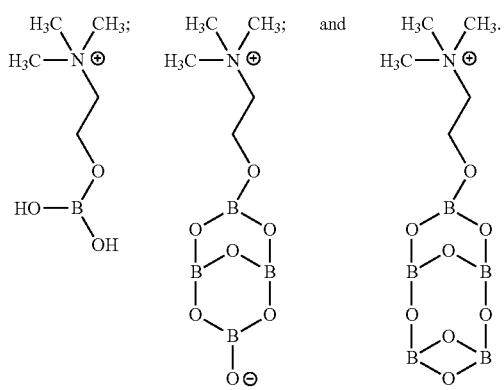

According to another embodiment, there is provided a pharmaceutical composition comprising a compound of the present invention, or a pharmaceutically acceptable salt thereof, and a pharmaceutically acceptable carrier.

According to another embodiment, there is provided a composition comprising a compound of the present invention, or a pharmaceutically acceptable salt thereof, and an acceptable carrier.

According to another embodiment, there is provided a use of a compound of the present invention or a pharmaceutically acceptable salt thereof for the manufacture of a medicament for treatment of a pathogenic infection in a subject.

According to another embodiment, there is provided a use of a compound of the present invention, or a pharmaceutically acceptable salt thereof, or the composition of the present invention, for treatment of a pathogenic infection in a subject.

The subject may be selected from the group consisting of a mammal, a fish, a bird, and a crustacean.

The mammal may be selected from the group consisting of a human, a bovine, an equine, and an ungulate.

The fish may be selected from the group consisting of a hagfish, a lamprey, a cartilaginous fish and a bony fish.

The bird may be selected from the group consisting of chicken, a turkey, and a fowl.

The crustacean may be selected from the group consisting of a shrimp, a crab, a lobster, a langouste.

According to another embodiment, there is provided a method of treating or preventing a pathogenic infection in a subject in need thereof comprising:
administering a therapeutically effective amount a compound of the present invention, or a pharmaceutically acceptable salt thereof, or the composition of the present invention, to said subject.

The subject may be selected from the group consisting of a mammal, a fish, a bird, and a crustacean.

The mammal may be selected from the group consisting of a human, a bovine, an equine, and an ungulate.

The fish may be selected from the group consisting of a hagfish, a lamprey, a cartilaginous fish and a bony fish.

The bird may be selected from the group consisting of chicken, a turkey, and a fowl.

The crustacean may be selected from the group consisting of a shrimp, a crab, a lobster, and a langouste.

According to another embodiment, there is provided a method of treating or preventing a pathogenic infection in a crustacean in need thereof comprising:
administering a therapeutically effective amount a compound of the present invention, or a pharmaceutically acceptable salt thereof, or the composition of the present invention, to said crustacean.

The crustacean may be selected from the group consisting of a shrimp, a crab, a lobster, and a langouste.

The pathogenic infection may be caused by a virus, a microorganism, or combinations thereof.

The virus may be one of more of White Spot Syndrome Virus (WSSV), Taura Syndrome Virus (TSV), Yellow Head Virus (YHV), Infectious Hypodermal and Haematopoietic Necrosis (IHHNV), Spherical *Baculovirus*, Spawner-isolated Mortality Virus Disease, Spring Viremia of Carp (SVC caused by Rhabdoviruses), Koi Herpes Virus (KHV), Large Mouth Bass Virus (LMBV), and *Baculovirus penaei* (BP).

The microorganism may be one or more of *Vibrio parahaemolyticus, Vibrio harveyi, V. splendidus, V. parahaemolyticus, V. alginolyticus, V. anguillarum, V. vulnificus, V. campbelli, V. fischeri, V. damsella, V. pelagicus, V. orientalis, V. ordalii, V. mediterrani, V. logei*, an Enterobacteriacae, *Clostridium botulinum, Listeria monocytogenes*.

The Enterobacteriacae may be one or more of an *Escheria coli*, a *Salmonella*, a *Shigella*.

Administering may be by feeding said compound, or said pharmaceutically acceptable salt thereof, or said composition to said crustacean.

The composition may be a dietary composition.

The composition may be for use in the treatment or prevention of a pathogenic infection in a crustacean in need thereof.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DEFINITIONS

Figure 1:
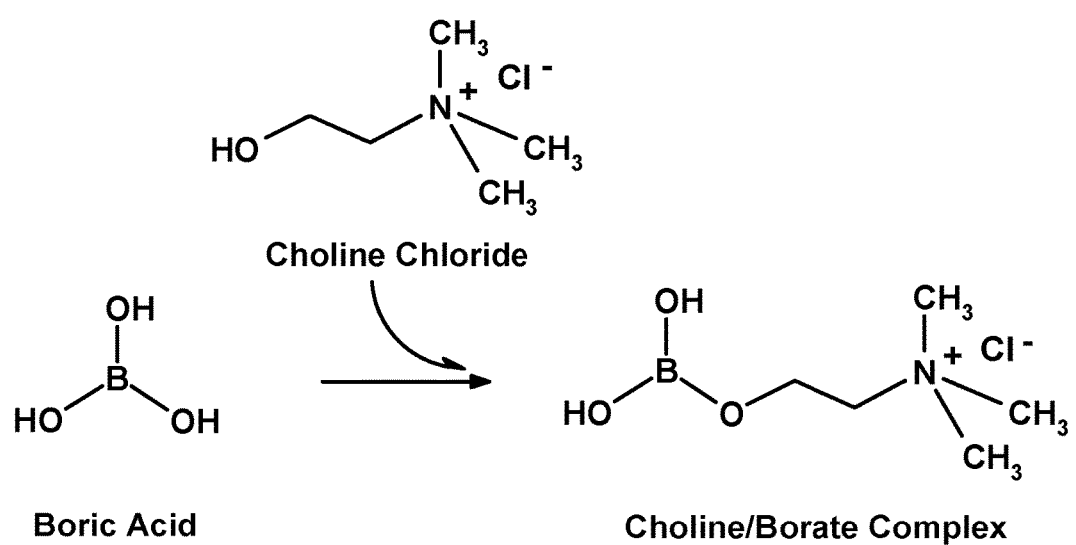
FIG. 1: illustrates the synthesis of choline/boric acid complex.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from C3-10, the term alkyl also includes cycloalkyl groups, and combinations of linear or branched alkyl chains combined with cycloalkyl structures. When no number of carbon atoms is specified, C1-6 is intended.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined Cycloalkanes consist of only carbon (C) and hydrogen (H) atoms and are saturated because there are no multiple C—C bonds to hydrogenate (add more hydrogen to). A general chemical formula for cycloalkanes would be $C_nH_{2(n+1-g)}$ where n=number of C atoms and g=number of rings in the molecule. For those cycloalkanes that have one ring in their molecules, cycloalkanes can be treated as isomers of their alkene counterparts, for example, cyclopropane and propene both have the chemical formula $C_3H_6$. Cycloalkanes with a single ring are named analogously to their normal alkane counterpart of the same carbon count: cyclopropane, cyclobutane, cyclopentane, cyclohexane, etc. The larger cycloalkanes, with greater than 20 carbon atoms are typically called cycloparaffins.

The term «composition» as used herein is intended to encompass a product comprising the specified ingredients in the specified amounts, as well as any product which results, directly or indirectly, from combination of the specified ingredients in the specified amounts. Such term in relation to pharmaceutical composition is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By «pharmaceutically acceptable» or «acceptable» it is meant the carrier, diluent or excipient must be compatible with the other ingredients of the formulation and not deleterious to the recipient thereof.

The terms "administration of", "administer" and/or "administering a" compound should be understood to mean providing, to dispense, to mete out, give to, a compound of the invention of the invention to the individual or subject in need of treatment by any suitable means, such as oral administration, parenteral, rectal, transdermal, etc. According to an embodiment for administration to crustacean, the compounds and composition of the present invention may be provided through the food administered to the subject.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Compounds of Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

DETAILED DESCRIPTION

In embodiments, there are disclosed compounds formed by the complexation of boric acid and its derivatives and quaternary ammonium compounds.

Boric Acid and its Derivatives

Boric acid and its salts were registered in 1983 for control of cockroaches, ants, grain weevils and several beetles. They were also used as herbicide, fungicide and wood preservative, even as an insect repellent in insulation. As an insecticide, boric acid acts as a stomach poison for ants, cockroaches, silverfish and termites, and as abrasive to the insects exoskeleton. As an herbicide, boric acid causes desiccation or interrupts photosynthesis in plants.

Boron is a naturally-occurring element in the earth's crust and background levels even circulate in the human bloodstream. According to United States Environmental Protection Agency (US EPA. 1993. Prevention, Pesticides, and Toxic Substances. EPA-738-F-93-006), boric acid and its salts will not pose unreasonable risks or adverse effects to humans or the environment. Available studies indicate that technical boric acid is practically nontoxic to birds, fish and aquatic invertebrates, and relatively nontoxic to beneficial insects. Moreover, the amount of boric acid and its salts used as pesticides are relatively small and significant lower than amounts of boron presented naturally in soil and water.

Borates that may be used in the present invention include but are not limited to orthoborate, metaborate, triborate, tetraborate, pentaborate, etc. or combination thereof. Also included are boric acid derivatives such as boronic acids (alkyl- (e.g. myristyl, palmityl, stearyl), alkenyl- or aryl-substituted boric acid such as phenyl boronic acid, 4 pyridine boronic acid, etc,) or organoborates (alkyl, alkenyl or aryl ester borate such as phenyl ester boric acid) or combination thereof.

Quaternary Ammonium Compound and Choline

Quaternary ammonium compounds (cations), also known as quats, are positively charged polyatomic ions of the structure $NR_4^+$, R being an alkyl group or an aryl group. Unlike the ammonium ion ($NH_4^+$) and the primary, secondary, or tertiary ammonium cations, the quaternary ammonium cations are permanently charged, independent of the pH of their solution. Quaternary ammonium salts or quaternary ammonium compounds (called quaternary amines in oilfield parlance) are salts of quaternary ammonium cations with an anion.

According to an embodiment, the quaternary ammonium compound is choline and derivatives thereof, which is a water-soluble nutrient, usually grouped within the B-complex vitamins, that plays key roles in many biological processes. Choline generally refers to the various quaternary ammonium salts containing the N,N,N-trimethylethanol ammonium cation. The cation appears in the head groups of phosphatidylcholine and sphingomyelin, two classes of phospholipid that are abundant in cell membranes. Choline is the precursor molecule for the neurotransmitter acetylcholine, which is involved in many functions including memory and muscle control. Choline must be consumed through the diet for the body to remain healthy. It is used in the synthesis of the constructional components in the body cell membranes. Despite the perceived benefits of choline, dietary recommendations have discouraged people from eating certain high-choline foods, such as egg and fatty meats. The 2005 National Health and Nutrition Examination Survey stated that only 2% of postmenopausal women consume the recommended intake for choline.

According to another embodiment, quaternary ammonium compound is preferably, but not limited to, choline chloride (2-hydroxyethyl trimethyl ammonium chloride) or its derivatives possessing on the alkyl chain at least a free hydroxyl group, i.e. (2-Hydroxyethyl) triethylammonium chloride, (2-hydroxypropyl)trimethyl ammonium chloride; (2,3-dihydroxypropyl)trimethyl ammonium chloride, etc.

Therefore, in embodiments, there is disclosed an antibacterial and antiviral compound based on borate or borate derivatives which are complexed with a quaternary ammonium.

In embodiments, there is disclosed a compound of formula I, or a pharmaceutically acceptable salts thereof, and stereoisomers thereof:

(I)

wherein $R^1$, $R^2$, $R^3$, and $R^4$ are independently selected from alkyl, cycloalkyl, or aryl, optionally substituted with one or more —OH, and each of the $R^1$, $R^2$, $R^3$, and $R^4$ may be optionally connected to another of the $R^1$, $R^2$, $R^3$, and $R^4$;

$R^5$ is selected from —$BO_2$, —$BO_3$, —$BO_4$, —$B_2O_3$, —$B_2O_4$, —$B_3O_5$, —$B_3O_7$, —$B_4O_7$, —$B_4O_9$—$B_5O_8$, —O—$BR^6R^7$, —$R^9$—$BR^6R^7$;

$R^6$ is selected from —H, —OH, alkyl, alkenyl, aryl, —O—$R^8$;

$R^7$ is absent or selected from —H, —OH, alkyl, alkenyl, aryl, and —O—$R^8$;

$R^8$ is selected from —H, alkyl, alkenyl, aryl;
$R^9$ is selected from alkyl, alkenyl, and aryl.

According to an embodiment, the $R^1$ may be C1-6 alkyl, linear or branched. According to an embodiment, the $R^1$ may be $CH_2$—$CH_2$.

According to another embodiment, the $R^2$, $R^3$, and $R^4$ may be C1-3 alkyl. According to another embodiment, the $R^2$, $R^3$, and $R^4$ may be independently $CH_3$, $CH_2$—$CH_3$, or $CH_2$—$CH_2$—$CH_3$.

According to another embodiment, the $R^5$ is —$B_5O_8$.

Indeed, according to an embodiment, boric acid or its derivatives complexed with choline are preferably used in the present invention, due to several advantages such as naturally occurring; low toxicity; inexpensive and easy to manufacture.

According to another embodiment, the compound of formula I, or a pharmaceutically acceptable salts thereof, and stereoisomers thereof, may be selected from the following compounds:

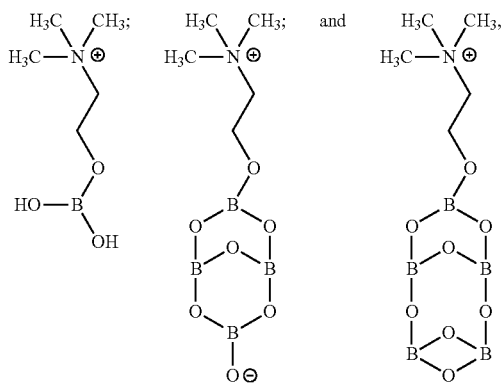

and combinations thereof.

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also be useful in treating pathogenic infections. Inactive or less active diastereoisomers and enantiomers are useful for scientific studies relating to the target pathogens and the mechanisms of action of the compounds of the present invention.

The compounds disclosed herein may be used in pharmaceutical compositions comprising (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound of Formula I or a pharmaceutically acceptable salt thereof is the only active ingredient.

The compounds disclosed herein may be used in compositions comprising (a) the compound(s) or acceptable salts thereof, and (b) an acceptable carrier. The compounds may be used in compositions that include one or more other active ingredients. The compounds may also be used in compositions in which the compound of Formula I or an acceptable salt thereof is the only active ingredient.

According to another embodiment, there is disclosed a use of a compound of the present invention, or a pharmaceutically acceptable salt thereof for the manufacture of a medicament for treatment of a pathogenic infection in a subject.

Also disclosed is the use of a compound of the present invention, or a pharmaceutically acceptable salt thereof, or the composition of the present invention, for treatment of a pathogenic infection in a subject.

According to another embodiment, there is disclosed a method of treating or preventing a pathogenic infection in a subject in need thereof comprising administering a therapeutically effective amount a compound of the present invention, or a pharmaceutically acceptable salt thereof, or the composition of the present invention, to the subject.

According to an embodiment, the pathogenic infection may be a bacterial infection, a viral infection, a fungal infection, a parasite infection, or a combination thereof. Examples of bacterial infections include but are not limited to Vibrionaceae infection, a Enterobacteriacae infection, a *Clostridium botulinum* infection, a *Listeria monocytogenes* infection. Examples of viral infection include but are not limited to a Taura Syndrome Virus (TSV) infection, a Yellow Head Virus (YHV) infection, a Infectious Hypodermal and Haematopoietic Necrosis (IHHNV) virus infection, a Spherical *Baculovirus* infection, a Spawner-isolated Mortality Virus Disease infection, a Rhabdovirus infection, a Koi Herpes Virus (KHV) infection, a Large Mouth Bass Virus (LMBV) infection, a *Baculovirus penaei* (BP) infection, Herpesviridae infection, a Retroviridae infection, a Filoviridae infection, and an HIV infection.

According to an embodiment, the subject may be a mammal, a fish, a bird, and a crustacean. The mammal may be a human, a bovine, an equine, an ungulate, etc. The fish may be a hagfish, a lamprey, a cartilaginous fish and a bony fish. Said bird may be a chicken, a turkey, a fowl. Said crustacean may be a shrimp, a crab, a lobster, a langouste, etc.

According to another embodiment, there is disclosed a method of treating or preventing a pathogenic infection in a crustacean in need thereof comprising administering a therapeutically effective amount a compound of any one of the present invention, or a pharmaceutically acceptable salt thereof, or the composition of the present invention, to the crustacean.

The present invention will be more readily understood by referring to the following examples which are given to illustrate the invention rather than to limit its scope.

These examples further illustrate the method of production of borate derivatives and method to complex with quaternary ammonium compound, preferably choline (2-hydroxyethyl)trimethyl ammonium chloride (FIG. 1).

EXAMPLE 1

Preparation of Choline/Borate Complex

The choline/borate complex (FIG. 1) is essentially prepared in saturated aqueous solution in order to facilitate obtaining the final product by crystallization at low temperature. The concentrations of choline and boric acid are preferably used in an equimolar ratio (1:1).

1-1—Complexation of Choline Chloride with Boric Acid

An amount of 123.66 g of boric acid is dispersed in 400 mL of distilled water at 90° C. The solution is under strong stirring. After dispersion of Boric acid, an amount of 279.24 g of choline chloride is slowly added in the boric acid solution and the temperature is maintained at 60° C. When choline chloride is added, the solution is cloudy, but become clear after 1 h heating, always under strong stirring (~600 rpm). The reaction is continued during at least 2 h.

1-2—Crystallization of the Choline/Borate Complex

At the end of the reaction, the temperature is gradually reduced in order to cool down slowly the solution, while gentle stirring (~200 rpm). When the temperature reached between 35-40° C., the solution is transferred in a plastic container and the stirring is reduced at 150 rpm to promote crystal formation. At this moment, some ice can be added into the water bath to accelerate the cooling-down processing. Once the temperature is about of 15° C., the solution is refrigerated between 4-6° C. for 24 hours. The crystals are then collected by decantation or by filtration using a 24-cm Whatman filter paper No 1 under a negative pressure (vacuum) about of 40 kPa. The collected crystals are dried in an oven at a temperature ranging from about 35-40° C. for at least 24 h.

EXAMPLE 2

Preparation of Choline/Tetraborate Complex

The complexation of choline and tetraboric acid is prepared under identical conditions as described previously in EXAMPLE 1, except that disodium tetraborate decahydrate is used instead of boric acid.

EXAMPLE 3

Preparation of Choline/Pentaborate Complex

The synthesis of choline/pentaborate complex could be prepared in two ways. Firstly, one approach consists in preparing first choline/borate complex which reacts with disodium tetraborate decahydrate to form choline/pentaborate complex. Alternatively, another approach consists in primarily synthesizing sodium pentaborate followed the complexing with choline.

Figure 2:
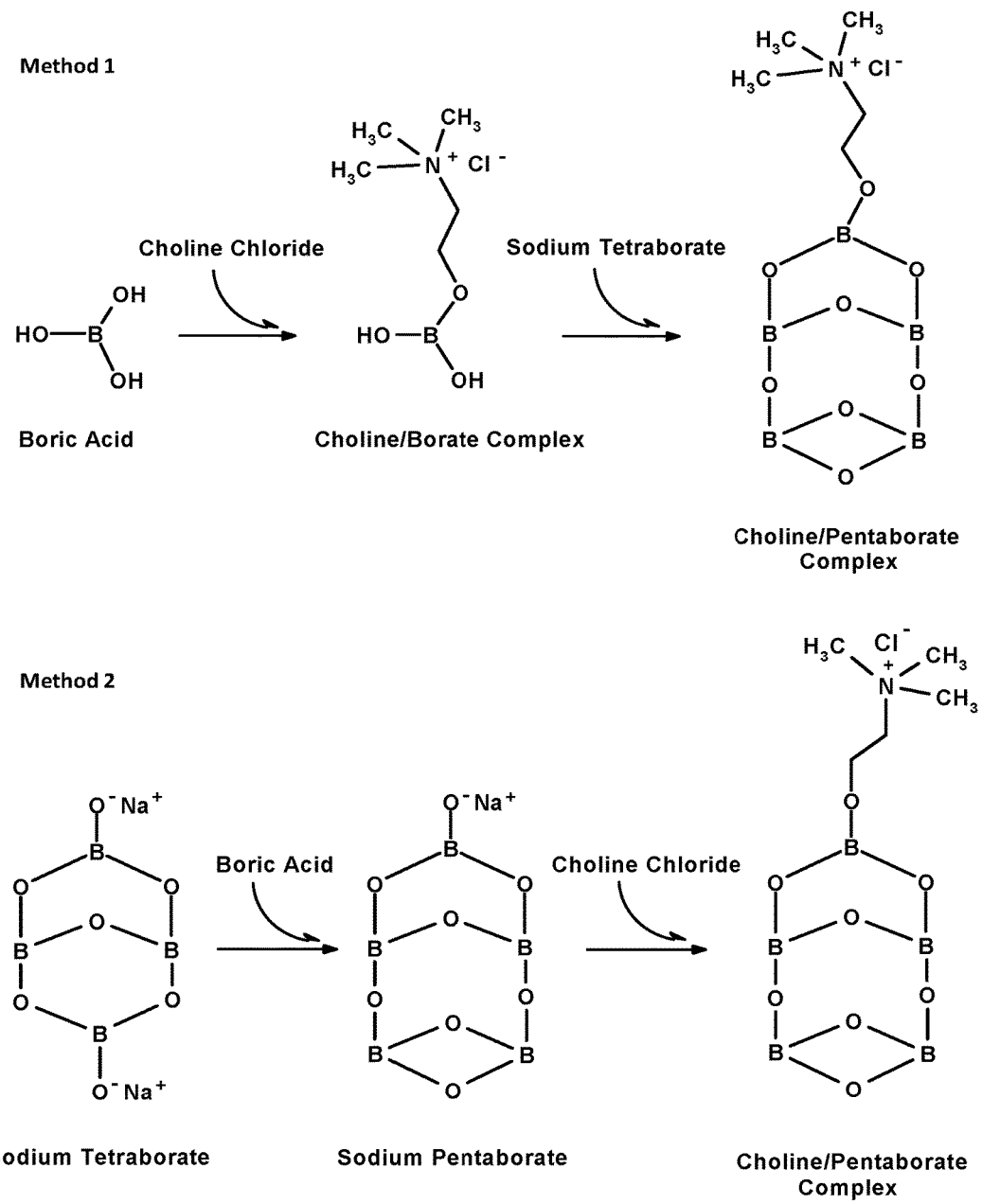
FIG. 2: illustrates the preparation of choline/pentaborate complex obtained by different synthesis methods.

3-1—Method I 3-1-1—Preparation of Choline/Borate Complex
The complexation of choline and boric acid is prepared under identical conditions as described previously in EXAMPLE 1 (FIG. 1).
3-1-2—Complexation of Choline/Borate with Disodium Tetraborate Decahydrate
When the reaction of complexation choline/boric acid is achieved, the temperature of the solution is reduced to about 60° C. Then, an amount of 127.39 g of disodium tetraborate decahydrate is added in the solution, under strong stirring in order to react with choline/boric acid previously obtained (FIG. 2, Method 1). After complete dispersion, the reaction is continued at least 2 h and the temperature of the solution is gradually reduced to room temperature and gentle stirring (150-200 rpm) to favor the crystallization. When the temperature has reached at room temperature, the solution is refrigerated for 24 h and choline/pentaborate crystals are collected by filtration and dried for 24 h at 40° C.

3-2—Method II 3-2-1—Preparation of Sodium Pentaborate
A volume of 800 mL of distilled water is introduced in a glass tempering beaker and heated at the temperature of about 60° C. When the set temperature is reached, an amount of 350 g of disodium tetraborate decahydrate and of 340 g of boric acid are introduced in the beaker alternately, portion by portion (approximately 20 g for each), under gentle stirring. Dissolution of all chemicals is ensured before adding the next portion, without stopping stirring.

Once all chemicals are completely added, the temperature of the solution is maintained at 60° C., always under stirring for at least 30 min. To obtain sodium pentaborate powders, the solution is slowly cooled down with moderate stirring (about of 200 rpm). When the temperature reaches 25° C., the solution is refrigerated at 4° C. during 24 h. The precipitate is collected by filtration in a plastic container and stored at 40° C. at least 24 h before use.
3-2-2—Complexation of Pentaborate with Choline
An amount of 300 g of sodium pentaborate crystals (previously obtained) is introduced in a glass tempering beaker containing 350 mL distilled water, under gentle stirring at a temperature 55±2° C. After completely dissolving, an amount of 140 g of choline chloride is slowly added in the pentaborate solution, always under stirring and the reaction is started for at least 1 h (FIG. 2, Method 2).

The choline/pentaborate complex crystals are obtained by refrigeration under identical conditions as described previously for preparation of sodium pentaborate. Indeed, the choline/pentaborate solution is slowly cooled down with moderate stirring (about of 200 rpm). When the temperature reaches 25° C., the solution is refrigerated at 4° C. during 24 h. The precipitate is collected by filtration in a plastic container and stored at 40° C. at least 24 h before use. The predicted structure of choline/pentaborate complex is presented in FIG. 2.

EXAMPLE 4

Characterization of Complex of Choline/Borate and its Derivatives

4-1—Determination of Quaternary Ammonium Compound in the Complex 4-1-1—Spectrophotometric Assay Based on Dragendorff Reagent
In order to estimate the quaternary ammonium compounds (QAC) of choline derivatives, a spectrophotometric assay based on Dragendorff reagent is used as described by Stumpf (Stumpf, D. K. 1984. *Plant. Physiol.*, 75, 273-274) with slight modifications. The principle consists in using bismuth nitrate and sodium iodide which form a complex and cause the precipitation of QAC with a development of a brick red color in the reaction medium. Practically, Dragendorff reagent is prepared by mixing equal volumes of bismuth nitrate 0.35 M in acetic acid 20% (v/v) and sodium iodide 2.45 M (in distilled water). Then, an amount of 100 µL of mixture is added in 10 µL of sample. The standard curve is made by placing 1.0-8.0 µL of a stock solution of choline (0.500 g/ml) into plastic 1.5 mL microcentrifuge tubes. Sample and standard solutions are centrifuged for 3 min at 10,000 g and the supernatants are completely removed. The obtained precipitates are then dissolved in 1 mL of 2.45 M NaI solution under strong stirring for at least 15 min and diluted by adding 99 mL of 0.49 M NaI. Finally, the samples are recorded by spectrophotometry at 420 nm (maximum absorption) using solution of 0.49 M NaI as a blank.

Generally, the quaternary ammonium compounds are detected in all samples which the ratio of choline/borate (tetraborate or pentaborate) complex is 1:1 (equimolar complex). No significant difference is observed for choline/pentaborate complexes obtained from method 1 and 2, as described in EXAMPLE 3.

4-1-2—Elemental Analysis

Analysis of the element compositions of choline/borate or its derivatives complexes allows confirming the structure of the complex formed between choline and different borate or its derivatives. No significant difference is observed between the ratio of choline/pentaborate obtained by the method 1 and 2, as described in EXAMPLE 3.

4-1-3—FTIR Analysis

FTIR spectra are recorded on a Spectrum One (Perkin Elmer, Canada) instrument equipped with a Universal Attenuated Total Reflectance (UATR) device. All samples including borate or its derivatives and borate or its derivative complexes are recorded under powder (20 mg) forms in the spectral region (4000-650 $cm^{-1}$) with 24 scans/min at a 4 $cm^{-1}$ resolution.

Figure 3:
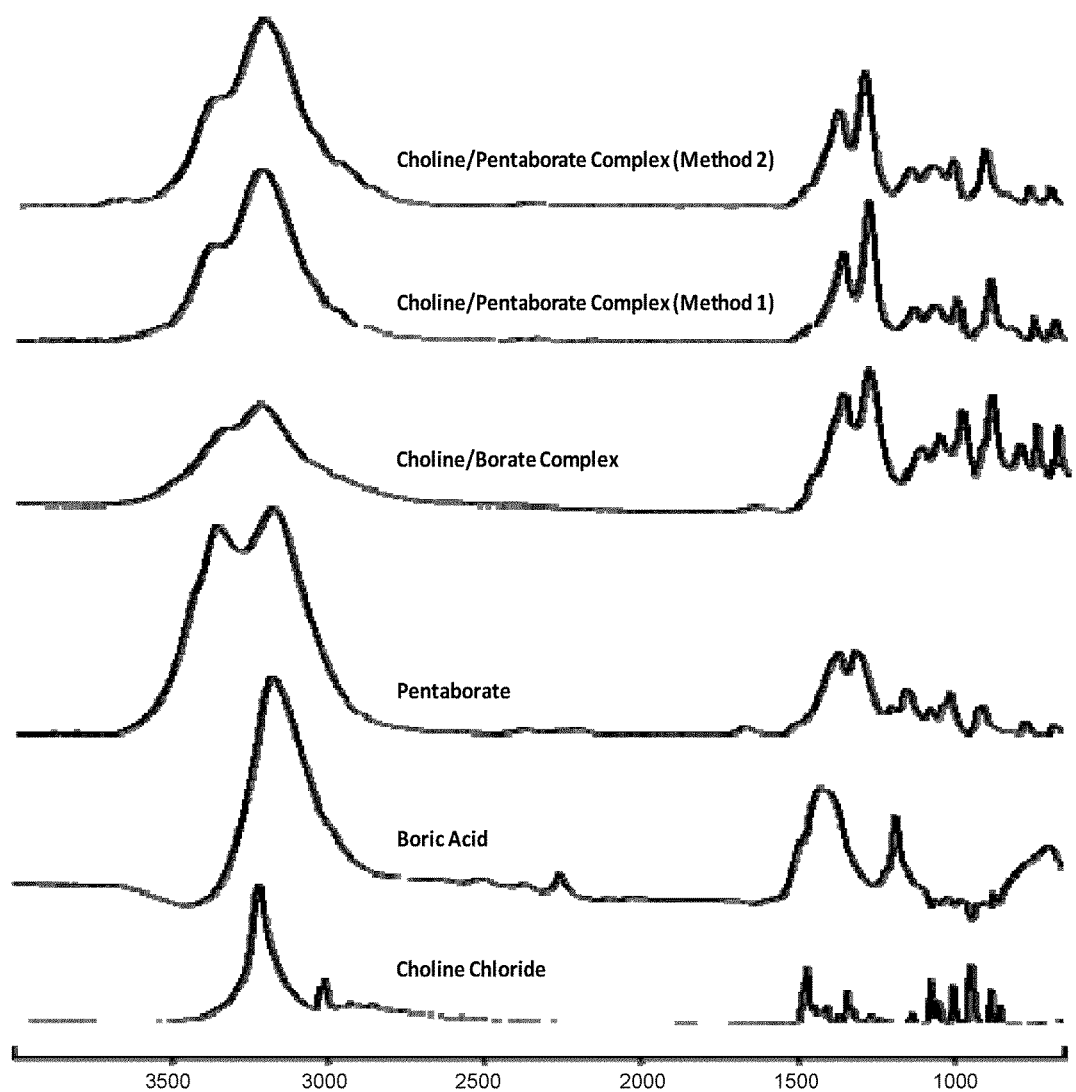
FIG. 3: illustrates FTIR spectra of choline chloride, boric acid, pentaborate and choline complexed with borate and pentaborate obtained by different synthesis methods.

FIG. 3 illustrates FTIR spectra of choline chloride, boric acid, pentaborate and choline complexed with borate and pentaborate obtained by different synthesis methods.

For planar boric acid FTIR spectrum, the stretching vibration of the B—O—H bands are observed at 3220 $cm^{-1}$. For absorption bands located at 1430 and 1195 $cm^{-1}$, they are respectively assigned for the asymmetric B—O stretching vibration and the in-plane B—O—H bending. With regard for pentaborate, similar observation for the stretching vibration of the B—O—H bands is noticed at 3220 cm-1. However, a new absorption band appeared at about 3380 $cm^{-1}$ and is possibly due to H—O—H (free O—H from water). Additionally, B—O absorption bands contributed for the asymmetric B—O stretching vibration and the in-plane B—O—H bending are shifted to 1375 and 1140 $cm^{-1}$. A new band also observed at 1300 $cm^{-1}$ and could be due to the B—O—B stretching vibration.

When boric acid or pentaborate are complexed with choline, similar FTIR spectral profiles are observed. In the spectral regions 3500-3000 $cm^{-1}$, the stretching vibrations of the O—H bands are observed at 3380 and 3220 $cm^{-1}$ which are respectively assigned for the absorption band of H—O—H and the absorption band of B—O—H. In the spectral region 1500-1000 $cm^{-1}$, the stretching vibrations for B—O are located at 1375 and 1300 $cm^{-1}$ and the in-plan B—O—H bending is noticed at 1140 $cm^{-1}$. A slight shoulder observed at 1410 $cm^{-1}$ seems to contribute to quaternary ammonium $CH_3$—$N^+$ (from choline). Also, the absorption bands at 1080 and 1010 $cm^{-1}$ are respectively attributed to C—N and C—O stretching vibrations.

EXAMPLE 5

Toxicity Evaluation of Choline/Borate and Choline/Borate Derivative Complexes for Shrimp *Litopenaeus Vannamei*

5-1—Collection and Maintenance of Experimental Animals

Shrimp, *Litopenaeus vannamei* (post-larvae about 12-16 day-old), are obtained from a commercial hatchery in La Paz (BCS, Mexico) and maintained in 1000 L fiber glass tanks with air-lift biological filters at room temperature in water with a salinity of 35 parts per thousand (ppt).

Natural seawater is used in all the experiments. It is obtained from the Ensenada de La Paz after removing the sand and other suspended particles in sea water. Finally, the seawater is sterilized with UV-lamp before use for the experiments. The tanks are individually aerated through air stones connected to a high-volume air blower. Partial water changes are made once a week to maintain the water quality. The shrimps are initially fed *Artemia* sp and are weaned onto a commercial diet (containing 35% crude protein, Purina Brand) when they reached 20 days of age (post-larvae 20 day-old). Daily, temperature and pH value are recorded; salinity is measured with a Salinometer (Aquafauna, Japan) and dissolved oxygen is estimated by the Winkler method (Strickland and Parsons, 1972).

5-2—Toxicity Evaluation of Choline/Borate and Choline/Borate Derivative Complexes White shrimp (*L. vannamei*) from intensive culture ponds are selected and acclimated to the experimental conditions during one week before starting the trial. Indeed, shrimp are placed in 1000 L circular tanks with filtered sea water at 38 parts per thousand (ppt) and constant aeration, fed ad libitum with a commercial pellet containing 35% crude proteins.

After the acclimatation period, different concentrations (1, 5 and 10 mg/g) of choline/borate or its derivatives are physically mixed with commercial pellet feeds and fed in the identical conditions (ad libitum) during 15 days. Globally, there are 6 groups are investigated in this study:

1. Boric acid;
2. Tetraborate;
3. Pentaborate;
4. Choline/borate complex;
5. Choline/tetraborate complex;
6. Choline/pentaborate complex.

Results show that there is no significant difference between group of control and groups treated with boric acid or its derivatives complexed with choline. These results suggest that no toxicity are apparent for white shrimp *L. vannamei* for doses of boric acid or its derivative complexes lower than 10 mg/g of shrimp feed.

EXAMPLE-6

Preparation for Challenge Studies 6-1—Preparation for Bacterial Assays 6-1-1—Bacterial Strains and Culture Conditions Virulent bacterial strains *Vibrio parahaemolyticus* CAIM 170 (Collection of Aquatic Important Microorganisms, CIAD, Mexico) are used in this study (Roque et al., 1998). These strains are maintained in Tryptone Soy Broth (TSB) containing 2.5% (w/v) NaCl and 15% (v/v) of glycerol at −80° C. Prior to use, a cryovial is thawed and inoculated into 5 mL of TSB with 2.5% (w/v) NaCl and incubated overnight at 37° C. in a rotary shaker (200 rpm) for activation. Thereafter, a volume of 2 mL of the overnight culture is transferred to 100 mL of TSB and reincubated in the similar activation conditions (37° C., 200 rpm).

Density of bacteria is measured by spectrophotometry at 600 nm for every 30 min. At the same time, an aliquot is withdrawn for viable count determination by plating serial dilutions on Tryptone Soy Agar with 1% NaCl. The plates are incubated for 24 h at 37° C. A growth curve was prepared by plotting the viable count (x-axis) against optical density at 600 nm values (y-axis). This graph was used to determine the viable cell count during further spiking studies. For the challenge, control groups are included in all trials:

A positive control group of shrimp is treated with pathogen *V. parahaemolyticus;*

A negative control group of shrimp, instead of receiving the pathogen, is treated with a sterile saline solution (without pathogens).

Preliminary trials showed that a *V. parahaemolyticus* (VP) suspension of 1×10⁶ colony-forming units (cfu)/mL could kill 60% of the shrimp population in 24 h and about of 70% in 96 h, whereas a group treated with a non-virulent *V. parahaemolyticus* strain showed the cumulative shrimp mortality at 96 h is less than 10%.

6-1-2—Optimization of Real-Time Polymerase Chain Reaction Assay for Quantitative Determination of *V. parahaemolyticus*

The primers used in this assay are Vp-ToxR q-PCR (*Vibrio parahaemolyticus* ToxR gene quantitative Polymerase Chain Reaction) 176 F (forward primer, SEQ ID NO:1: GGA AGT TTT AAC CCG TAA CGA GC) and 176 R (reverse primer, SEQ ID NO: 2: GGT ACA AAT GAG TTG ATA GCC TCG) and designed as described by Untergasser et al. (2007) using the software «Primer3Plus», with the following parameters:

Primer length: 18-24 bp;
GC content: 35-65%;
Melting Temperature (Tm): 58° C.–60° C.;
Product size: 80-250 bp (Wang, X. and Seed, B. 2007. In: «Real-time PCR». Dorak M. Tevfik. Ed. Taylor & Francis. New York. USA. p. 93-105).

Thermodynamic parameters of each primer are evaluated to check primer-dimer and secondary structure using the software «Oligoevaluator» (Sigma-Aldrich™) and «Primer digital» (Kalendar, R., Lee, D., Schulman, A. H. 2011. Genomics, 98, 137-144). These primers yielded a 176 bp amplicon and are suspended in nuclease free water to make a working solution of 10 pmol/μL.

To establish the standard curve, serial dilutions are done with the DNA extracted and purified from culture of *V. parahaemolyticus* CAIM 170 using the following mixture:

5 μL of SSO-Fast supermix evagreen (BIORAD, USA);
1 μL of Vp-ToxR q-PCR 176F (10 pmol/μL);
1 μL of Vp-ToxR q-PCR176R (10 pmol/μL);
2 μL of DNAse-free water and 1 μL of template as DNA.

Quantitative PCR is performed on a Rotor gene 6000 Real-Time PCR system (Qiagen™). Amplification conditions are carried out as follows:

initial activation at 50° C. for 2 min;
initial denaturation at 95° C. for 10 min and followed by 45 cycles of denaturation at 95° C. for 15 s
primer annealing at 60° C. for 20 s and elongation at 72° C. for 30 s and a final elongation at 72° C. for 5 min.
A melting curve analysis is performed at the end of the amplification using the following conditions: 65° C.–80° C. (1° C./s).

The data are analyzed using the software Rotor Gene-Q Pure Detection (1.7 Build 94).

6-1-3—Enrichment Media and Samples for Detection of *V. parahaemolyticus*

In this study, an enrichment medium is used to evaluate their effect on detection of *V. parahaemolyticus*. The enrichment medium used is alkaline peptone water (APW; 1% peptone, 1% NaCl, pH 8.5; Tyagi et al., 2009). Practically, an amount of 5 g of shrimp is collected and placed on ice. Immediately, these shrimp are homogenized in phosphate buffer at pH 7.5 with a Polytron homogenizer, under sterile conditions. A volume of 1 mL of homogenized material is inoculated in APW medium and incubated overnight at 37° C. for 24 h in a rotary shaker at 200 rpm.

6-1-4—*V. parahaemolyticus* DNA Extraction from APW Medium

A volume of 1 mL of APW medium is collected in a microcentrifuge tube. The tube containing medium is centrifuged at 10,000 g for 10 min and the pellet is collected and washed with miliQ sterile water and suspended in 400 μL in miliQ sterile water. Further centrifugation at 10,000 g for 5 min and the tubes are incubated at 98° C. for 20 min before centrifuged at 5,000 g for 5 min. The supernatant is collected in a new microcentrifuge tube and stored at −20° C.

6-2—Preparation for White Spot Syndrome Virus (WSSV) Assays 6-2-1—WSSV Stock and In Vivo Titration The virus is isolated from WSSV-infected adult *L. vannamei* shrimp obtained from commercial farms located in Sinaloa, Mexico in 2013. Virus stocks were purified from infected shrimp homogenates by improved differential centrifugation as described previously by Du et al. (Du, H. H., Fu, L. L., Xu, Y. X., Kil, Z. S., Xu, Z. R. 2007. Aquaculture, 262:532-534) and then stored at −80° C. For assays, the WSSV stock is serially diluted to prepare solutions containing various target copy numbers determined by competitive PCR.

A volume of 20 μL of different dilutions of the tissue homogenate (containing WSSV in 330 mM of NaCl) is injected intramuscularly in fourth or fifth abdominal segment of *L. vannamei* using an insulin needle. The mortality is recorded twice a day and dead shrimp are tested by PCR to highlight the presence of WSSV.

A dilution of WSSV containing 1×10⁶ copies is appropriated to use in subsequent experiments (Du et al. 2006). In the present study, this dilution containing 1×10⁶ copies is approximately corresponding to 3% of WSSV suspension which can kill 50% of shrimps in 48 h, and 100% of shrimps in 96 h; on the other hand, a virus dilution at 1% of WSSV suspension can kill 80% of the shrimps in 120 h.

6-2-2—Detection of WSSV Using q-PCR Technique

After 48, 72 and 96 h after infection, haemolymph is collected from the ventral sinus using a sterile syringe containing 500 μL of anticoagulant solution (pH 7.3, at 4° C.) as described by Vargas-Albores et al. (Vargas-Albores, F., Guzman, M. A., Ochoa, J. L. 1993. *Compa. Biochem. Physiol.*, Part A, 106, 299-303):

450 mM NaCl;
10 mM KCl;
10 mM HEPES;
10 mM EDTA

The collected haemolymph is centrifuged at 12,000 g for 20 min at 4° C. and the precipitate is resuspended in TRIzol Reagent™. According to the manufacturer's instructions, total RNA is extracted and the pellets of total RNA are resuspended in 15 μL of RNAse free water. Total RNA is quantified using Nanodrop™ 1000 (Thermoscientific) using an amount of 1 μg of total RNA treated with DNAse I (Invitrogen™). The cDNA synthesis is performed using «Go Script Reverse Transcription System» (Promega). The sequence of used primer WSV230F is SEQ ID NO:3: GCT GGT GGG GGA TGA TAC TA, and that of primer WSV230R is SEQ ID NO:4: GTC TCC CGT CAC CGT CTT TA, as described by Gomez-Anduro et al. (Gomez-Anduro, G. A., Barillas-Mury, C. V., Peregrino-Uriarte, A.

B., Gupta, L, Gollas-Galvam, T., Hernandez-Lopez, J., Yepiz-Plascencia, G. 2006. *Develop. Comp. Immunol.*, 30: 893-900). The q-PCR is performed as follows:
- 5 µL of SSO-fast qPCR supermixes evaGreen (BIORAD, USA);
- 1 µL of WSV230F (10 pmol/µL) and 1 µL of WSV230R (10 pmol/µL);
- 2 µL of DNAse-free water;
- 1 µL of template as cDNA from hemocytes.

Initial denaturation at 95° C. for 10 min followed by 40 cycles of denaturation at 95° C. for 15 s, primer annealing at 58° C. for 20 s, elongation at 72° C. for 30 s and a final elongation at 72° C. for 5 min. A melting curve analysis is performed at the end of the amplification using the following conditions: 70° C.-95° C. (1° C./s). The data is analyzed using the software Rotor-Gene-Q Pure Detection (1.7 Build 94).

6-3—Challenge Studies 6-3-1—Experimental System

A static experimental system is used in consisting of 24, 20-1 fiber glass tanks. Each tank containing filtered and UV-sterilized seawater (at 35 ppt, pH 8.0) is individually aerated by an air stone at 27° C.

6-3-2—Experimental Procedure 6-3-2-1—Acclamation

An amount of twenty (20) shrimp are introduced to each tank filled with 30-L of UV-sterilized seawater. The shrimp are left to adapt to the system (acclamation) during 2 days. Shrimp is fed with pelletized commercial feed mixed with different quantities of choline/pentaborate complex during 28-days for further challenges with WSSV and a pathogenic *Vibrio parahaemolyticus* strain.

6-3-2-2—Challenge Test

The shrimp are either challenged in triplicate by injection with a known concentration of White Spot Syndrome Virus (1-3% viral suspension) or a pathogenic *Vibrio parahaemolyticus* ($1\times10^6$ cfu/mL) strain. There are two control groups:
1. Positive control groups—Shrimp that are not previously exposed with any borate or its derivatives and are either injected with a known concentration of WSSV or pathogenic VP;
2. Negative control groups—Shrimp are not fed with borate or its derivatives and are not treated with any pathogens; however, shrimp are injected with a saline solution, instead pathogens.

After the pathogen challenge, treated and control shrimp groups continued receiving the corresponding feed. The shrimp mortality percentage is recorded daily. Shrimps are observed for 96 to 120 h after each challenge and recorded water temperature and mortality. Shrimp samples are taken on the first day, during challenge and 72 h post-challenge. All shrimp samples are stored at −80° C. in RNA latter for further q-PCR analysis of pathogen loadings and expression of immune related genes.

6-3-2-3—Determination of Mortality Shrimp

Dead shrimp are recorded daily during 120 hours. All dead shrimp samples are stored at −80° C. in RNA latter for further q-PCR analysis of pathogen loading and expression of immune related genes.

Figure 4:
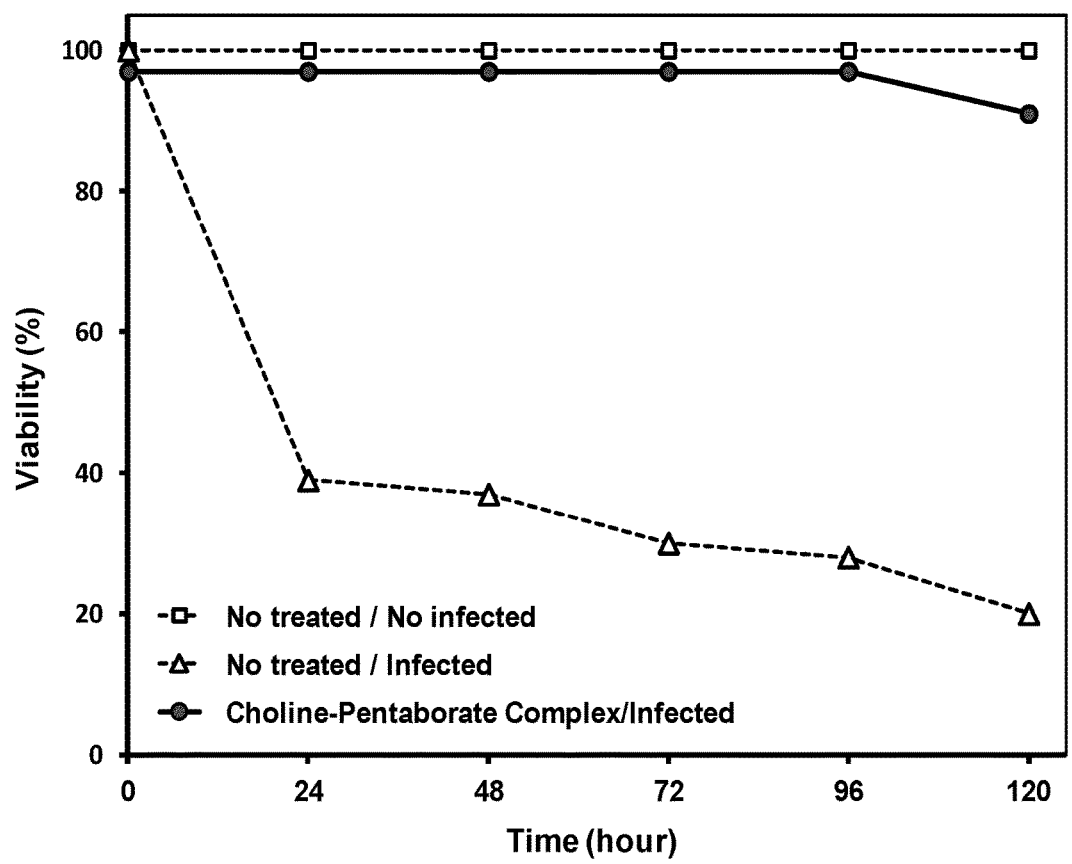
FIG. 4: Percentage of viability (%) of shrimps L. vannamei treated with feed containing choline/pentaborate complex (5 mg/g) after infection with Vibrio parahaemolyticus.

6-4—Results of Challenge Studies with Boric Acid or its Derivatives Used Alone or Complexed with Choline Shrimp challenged with virulent *V. parahaemolyticus* (FIG. 4) showed after 96 h that the shrimp survivals for the negative (not infected with pathogen and not treated with any borate complexes) control group are 100%. For positive (pathogen infected, but not treated with any borate complexes) control group, the survival rate is about 30%. Similar survival rate for borate, tetraborate or pentaborate (not complexed with choline) are observed at different doses (1, 5 and 10 mg/g of commercial pellets).

In contrast, high survival rates (>60%, p<0.05) are observed for choline/borate, choline/tetraborate and choline/pentaborate complexes.

Similar observation for shrimp challenged with WSSV (infected with 1% of WSSV suspension homogenate), the shrimp survival for the negative (not infected with pathogen and not treated with any borate complexes) control group are 100% after 96 h. For positive (pathogen infected, but not treated with any borate complexes) control group, the survival rate is about 30%. Similar survival rate for borate, tetraborate or pentaborate (not complexed with choline) are observed at different doses (1, 5 and 10 mg/g of commercial pellets). In contrast, high survival rates (>60%) are observed for choline/borate, choline/tetraborate and choline/pentaborate complexes.

It is worth mentioning that for all complexes tested with *V. parahaemolyticus*, the best survival (>80%) results are obtained with choline/pentaborate complex supplemented at dose of 5 mg/g of commercial pellet feed. Consequently, the choline/pentaborate complex is selected for subsequent studies.

6-4-1—Results of Choline/Pentaborate Complex Challenged with *Vibrio parahaemolyticus*

For shrimp infected with *V. parahaemolyticus* ($1\times10^6$ cfu/mL) and treated with choline/pentaborate complex at dose 5 mg/g of feed, the survival (FIG. 4) is 84% (p<0.01) after 96 h, whereas the survival of shrimp infected with *V. parahaemolyticus* and not treated with choline/pentaborate is about 30%.

6-4-1—Results of Choline/Pentaborate Complex Challenged with WSSV

There are no statistical differences between replicates for the same treatments (p>0.05), as the standard deviation between samples is lower than 3%.

Results show that there are statistical differences in shrimp challenged with a 3% WSSV suspension. Survival after 48 hours for shrimp from the positive control (infected) is about of 80% and for shrimp fed with choline/pentaborate complex at dose 5 mg/g is 95% survival (statistically different p<0.05). After 96 h post-challenge, only 10% of the positive control shrimp are alive. There is a marginal improvement for shrimp fed with choline/pentaborate complex at doses the 1 and 5 mg/g, where the survivals rates are about of 40%.

Figure 5:
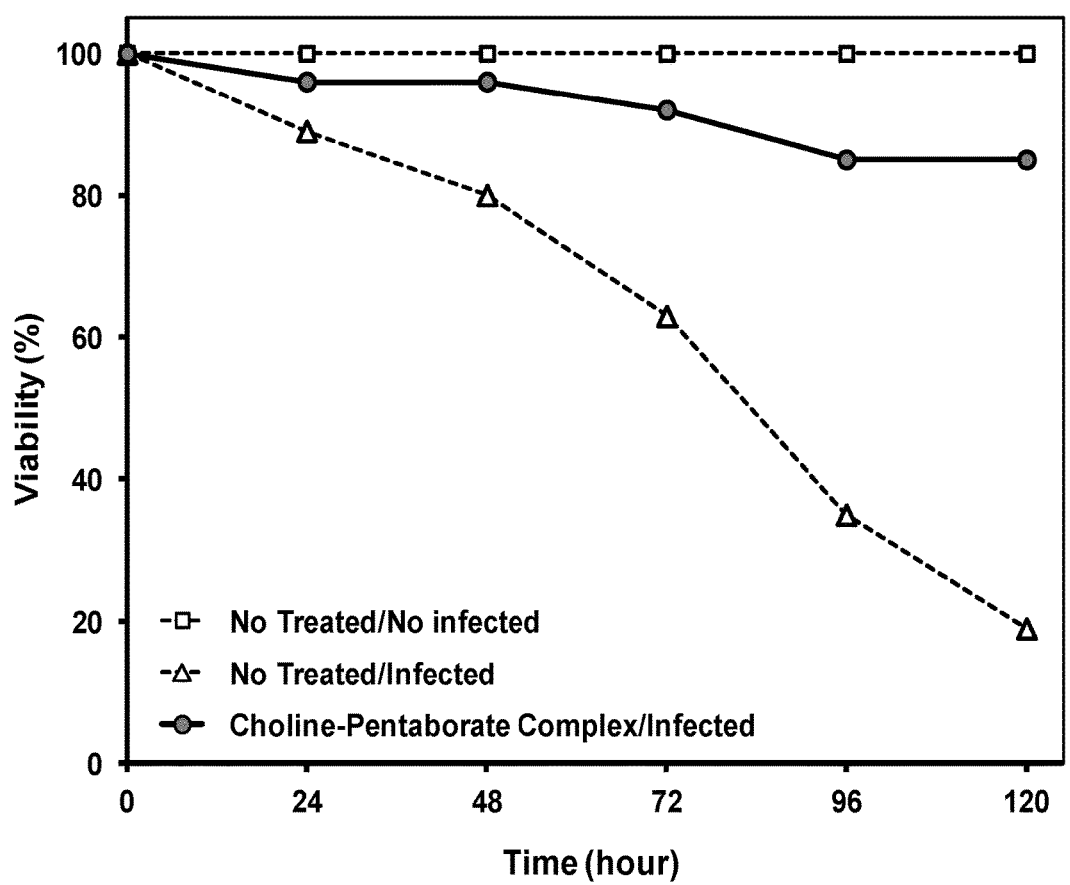
FIG. 5: Percentage of viability (%) of shrimps L. vannamei treated with feed with choline/pentaborate complex (5 mg/g) after infection with white spot syndrome virus (WSSV) homogenates.

In contrast, when shrimp are challenged with 1% WSSV suspension (FIG. 5), there is a statistical difference in survival (p<0.05). After 72 h, shrimp from the positive control (infected) had about of 65% survival whereas shrimp fed with 5 mg of choline/pentaborate complex/g of feed had 95% survival. After 96 h post-challenge, about 35% survival for shrimps in the positive control and 85% survival for shrimp fed with 5 mg of choline/pentaborate complex by gram of feed (p<0.05).

The use of functional feeds that contain antipathogenic compounds is considered fundamental in the strategy to prevent early infectious diseases in shrimp, such as Early Mortality Syndrome (EMS) and White Spot Syndrome Virus (WSSV). Further, some antimicrobial compounds, such as the ones tested in this trial, appear to be able to disrupt bacterial communication that activate certain genes associated to the release of toxins. This quorum quenching represents a significant alternative to the use of antibiotics.

Data analysis shows that the choline/pentaborate complex formulation supplemented at a 5 mg/g in feed diets is effective in reducing impact of WSSV infection when following standardized injection protocols. This represents a major breakthrough for the control of a disease that affects a significant number of commercial shrimp production operations, from hatcheries to grow out facilities. Though several products have been developed to prevent and treat WSSV, such as genetic vaccines, these have proven ineffective in commercial operations, impractical to apply for lack of effective delivery mechanisms, or expensive. Choline/pentaborate complex is not toxic, simple to manufacturing, stable, easy to administer and relatively inexpensive.

The use of choline/pentaborate complex as additive in commercial diets provides an efficient mechanism for microbial activity control in the shrimp gut that may contribute to the solution of the mass mortalities associated to *V. parahemolyticus* and WSSV in commercial shrimp farms.

EXAMPLE-7

Highlighting of Expression of Immune Related Genes in Shrimp *Litopenaeus Vannamei* by Choline/Pentaborate Complex

7-1—RNA Extraction

RNA is extracted using TRIzol® and the Qiagen RNeasy® Mini Kit (Qiagen, Germantown, Md., USA). Shrimp samples immersed in TRIzol® are placed in the FastPrep®-24 (MP Biomedicals LLC, Solon, Ohio, USA) and homogenized during 4° C. for 40 s pulses at 6 m/s. A volume of 200 μL of chloroform is added to a 1.5 mL RNase free tube containing the homogenate material and inverted 15 times. Samples are incubated at room temperature for 3 min before centrifuged at 8000 g for 15 min at 4° C. using the Eppendorf centrifuge. The supernatant is carefully transferred into a new 1.5 mL RNase free tube and the extraction continued following the manufacturer's protocol.

7-2—Assessing RNA Quality and Quantity

The quality and quantity of RNA are determined by the NanoDrop™ 1000 spectrophotometer (Thermo Fisher Scientific, Waltham, Mass., USA) and Bio-Rad™ (Bio-Rad, Hercules, Calif., USA) using denatured gel electrophoresis with formaldehyde and buffer MOPS 1× (Sambrook, J. 1989. in: «Molecular cloning—a laboratory manual, 2nd ed». J. Sambrook, E. F. Fritsch, T. Maniatis Eds. Cold Spring Harbor, N.Y.: Cold Spring Harbor Laboratory Press).

7-3—Microarray and Scanning

Microarrays are designed based on publically available gene sequences and ESTs determined from cDNA libraries representing multiple tissues of male and female *L. vannamei* shrimp, and/or of various physiological conditions.

In total, a length of oligonucleotides about of 61440-mer is included in this study: 39592 shrimp ESTs; 1216 Quality control spots; 112 positive control Alexa-555 dye; 80 positive control Alexa-647 dye; 20320 Unigenes; 16 astringent positive control alexa-555; 16 astringent positive control Alexa-647 dye and 88 negative control empty are submitted to the MYcroarray (University of Michigan, Chemical Engineering Department) for printing on aminosaline glass slides. The exposure and reference sample RNAs are adjusted to final volume 19 μL with oligo d(T) (2 μg/μL) and random primers (1 μg/μL) in water molecular biology grade. The samples are incubated at 70° C. for 10 min and are then chilled in ice. The samples are mixed finally with 5× Reaction Buffer Superscript II kit (Invitrogen, Life technologies, Carlsbad Calif., USA): 25 mM $MgCl_2$; aminoallyl-dNTP with dUTP (3:1); 0.1 M DTT and 200 U/μL Superscript II Reverse Transcriptase. The mix is incubated at 25° C. for 10 min and then at 42° C. for 2 hours. RNA hydrolysis is made with 5 μL of NaOH 1 N and 1 μL of EDTA 0.5 M. The mixture is incubated at 65° C. for 10 min, and then added 25 μL of HEPES 1 M at pH 7.5. The choline/pentaborate complex exposed samples (n=6) are labeled with Alexa-647 dye Molecular Probes™ (Life Technologies, Eugene Oreg., USA) fluorescent dye and the reference samples (n=6) are labeled with Alexa-555 dye Molecular Probes™ (Life Techynologies, Eugene Oreg., USA). The aminoallyl-DNA (aa-DNA) is purified using QIAquick™ (Qiagen, Duesseldorf, Germany). A volume of 7 μL of sodium acetate 3 M and 400 μL binding buffer supplied by the Kit are added. The mixture is allowed to stand 5 min according to the manufacturer's instructions for purification. The eluted aa-DNA is concentrated in a Vacufuge™ until dry and is resuspended in 4.5 μL of sodium bicarbonate 100 mM (pH 9.0). The reaction is conducted in darkness at room temperature overnight. The aa-DNA labeled is purified using QIAquick™ (Qiagen, Duesseldorf, Germany) and eluted with 50 uL water. The aa-DNA labeled is quantified in a Nanodrop™ 1000 spectrophotometer (Thermo Fisher Scientific, Waltham, Mass., USA).

After completely drying in a Vacufuge concentrator, the aa-DNA labeled is resuspended in hybridation mixture containing: ~0.1 optical density units of aa-DNA labeled from each sample; SSC (5×) buffer; 0.1% SDS; 1× buffer TE. The hybridation mixture is denaturated at 94° C. for 5 min and finally at 65° C. for 30 s. The mixture is placed in the microarray slide previously placed in a chamber for microarray hybridization and covered using a RNase-free plastic coverslip (Hybrislip, Schleicher & Schuell, HS40—40×22 mm; HS22—22×22 mm via Thomas Scientific). The hybridation chamber is incubated at 42° C. overnight.

The slide is placed in a 50 mL conical tube for the first wash and a volume of 50 mL of SSC (1×) buffer and of SDS 0.05% are added for 1 min. The washing is repeated twice using a volume of 50 mL of SSC (0.06×) for 2 min. The slide is centrifuged at 1500 rpm during 5 min.

The microarray slide is scanned in GenePix® 4100A Microarray Scanner (Molecular Devices, Silicon Valley, Calif., USA) at 5 μm resolution on the channels PMT 647 and PMT 555. The data of the scanning is analyzed in GenArise v2.7 software to obtain the data of select genes that are significantly differentially expressed onto control and treated samples. The genes are classified into categories and assigned a numerical value «zScore» base in the data normalization. The EST, Nucleotide and Unigenes sequences from the microarray are downloaded using «Batch-Entrez» at http://www.ncbi.nIm.nih.gov/sites/batch-entrez and loaded in Blast2GO as FASTA files (Conesa, A., Götz, S., García-Gómez, J. M., Terol, J., Talon, M., & Robles, M. 2005. *Bioinformatics,* 21, 3674-3676), performing a BlastX using an e-Value of $1\times10^3$ against Non-Redundant Database and functional annotation from gene ontology Database.

7-4—Analysis of Genes by RT-qPCR

RT q-PCR is performed on the 8 samples of shrimp treated with choline/pentaborate complex and a similar number of samples of shrimp non-treated for the microarray analysis (n=16) in order to validate 7 genes of interest (GOIs) and 3 reference genes. Primer of manganese superoxide dismutase (MnSOD) [Lv MnSOD q-PCR 149F (forward primer, SEQ ID NO: 5: GGG CTT CAT TAA CAA CCT AAT TGC), and Lv MnSOD q-PCR 149R (reverse primer, SEQ ID NO: 6: GGG CTT CAT TAA CAA CCT AAT TGC)]; and reference gene ribosomal protein L8 [Lv L8pro q-PCR 166F (forward primer, SEQ ID NO: 7: TAG GCA ATG TCA TCC CCA TT) and Lv L8pro q-PCR 166R (reverse primer, SEQ ID NO: 8: TCC TGA AGG AAG CTT TAC ACG)] are taken from Gomez-Anduro et al. (2006). Primer design is performed in the online application «primer3plus» (Untergasser, A., Nijveen, H., Rao, W., Bisseling, T., Geurts, R., Leunissen, J. A. M. 2007. *Nucleic Acids Research*, 35: 71-74) based in the following features: 18-24 nt length; GC content 35-65% product size 80-250 bp; and ≤2 GC clamp (Wang, X. and Seed, B., 2007). The primers are evaluated in the online application «Oligo Evaluator» Sigma Aldrich™ (St'Louis, Mo.) to check thermodynamic characteristics based in self-aligned primer and primer-dimer structures. The primers selected are ≤-2 Kcal/mol and evaluated using an in sillico PCR software «Primer Digital» (Kalendar et al., 2011). RNA extracts used for the microarray hybridizations are converted to cDNA using promega GoScript™ Reverse Transcription System (Promega Corporation, Madison, Wis., USA) and SsoFast™ EvaGreen® Supermix (Bio-Rad, Hercules, Calif., USA) for RT-qPCR. Fluorescence is detected by using the Rotor gene 6000 Real-Time PCR detection system (Corbette). A three-step cycling protocol is used with primer specific annealing temperatures. The RT q-PCR cycle is 95° C. for 10 min; followed by 40 cycles of 95° C. for 15 s and 20 s at the primer specific annealing temperature (see Table 1); 72° C. for 25 s after which the plate is read. The annealing temperature range for the primers is 56-62° C. Melt curve analysis is performed to determine product specificity over the temperature range of 65-95° C. in 1° C. increments and read every 5 s. The same six samples treated and non-treated shrimps (n=12) used for microarray are assayed in triplicate for RT q-PCR, in addition to triplicates of negative RT controls and negative template controls (NTC). The geNorm software (Vandensompele et al., 2002) identified 3 genes: β-actin, elongation factor 1-α and ribosomal protein L8 to be the most stable and meeting the selection criteria of M value of <1.25, representing the average expression stability and V value ≤1.5, indicating pair wise variation.

The other primers are:

Ferritin: Ferritin Forward,
SEQ ID NO: 9:
CAAGCGAACCTCTGGAAATC,
and

Ferritin Reverse,
SEQ ID NO: 10:
TGGCAAATCCAGGTAGAGC.

Toll-like receptor: LvToll Forward,
SEQ ID NO: 11:
GCCCTAAATGATGGATGAC,
and

LvToll Reverse,
SEQ ID NO: 12:
GCCAAGGGAAAAAGAAAT.

Elongation Factor 1-a: LvEF1A Forward,
SEQ ID NO: 13:
CCACACTGCTCACATTGC,
and

LvEF1A Reverse,
SEQ ID NO: 14:
GAAGGTCTCCACGCACAT.

B-Actin: LvACTB Forward,
SEQ ID NO: 15:
TGGGACGACATGGAGAAG,
and

LvACTB Reverse,
SEQ ID NO: 16:
GGGGGTGTTGAAGGTCTC.

Pre-amylase 1: LvPAMY Forward,
SEQ ID NO: 17:
CCGTCTCCTATAAACTCGTCACTC,
and

LvPAMY Reverse,
SEQ ID NO: 18:
TCGCCGTAGTTTTCAATGTTC.

Trypsinogen 1: LvTry Forward,
SEQ ID NO: 19:
TCGTCGGAGGAACTGACG,
and

LvTry Reverse,
SEQ ID NO: 20:
TGCCCTCATCCACATCCT.

Lipase Digestive 1: LvLIP Forward,
SEQ ID NO: 21:
TCCTGGCTCACACACCTG,
and

LvLIP Reverse,
SEQ ID NO: 22:
GTCCTTCAGCGAGCCTTG.

Cathepsin L: LvCPL Forward,
SEQ ID NO: 23:
CGTCCTTCCAGTTCTACCAT,
and

LvCPL Reverse,
SEQ ID NO: 24:
ATCTGGATGTAGCCCTTGTT.

7-5—Statistical Analysis

At termination of the exposure experiment, survival and mortality data are analyzed using TOXSTAT probit (adapted from Stephan, 1977) analysis software to calculate a $LC_{50}$ with a 95% confidence interval. Microarray gene expression values are analyzed using a one-way ANOVA and 100 permutations to detect significantly at p-value of 0.05. A Tukey post-hoc test is also used to identify significantly differentiated genes affected by the choline/pentaborate complex treatment. A user defined k-means cluster analysis (n=4) is run with a Pearson centered distance matrix and 100 iterations using GeneSpring (Agilent, Mississauga, ON, Canada). The mean CNRQ values from the RT q-PCR analysis of GOI for treated and non-treated shrimps are compared to identify significant differences in relative abundance using a one-way ANOVA with multiple test corrections and significant p-value<0.05. The CNRQ values are log 2 transformed and compared to microarray log 2 transformed expression ratios.

7-6—Results for Analysis of Genes by RT q-PCR 7-6-1—Treatment of *L. vannamei* Shrimp with Choline/Pentaborate Complex The two shrimp groups fed with a commercial feed (control group), and the other group, fed with the same commercial feed, but supplemented with choline/pentaborate complex at dose 5 mg/g of feed are maintained in the bioassay laboratory for up to 28 days.

Figure 6:
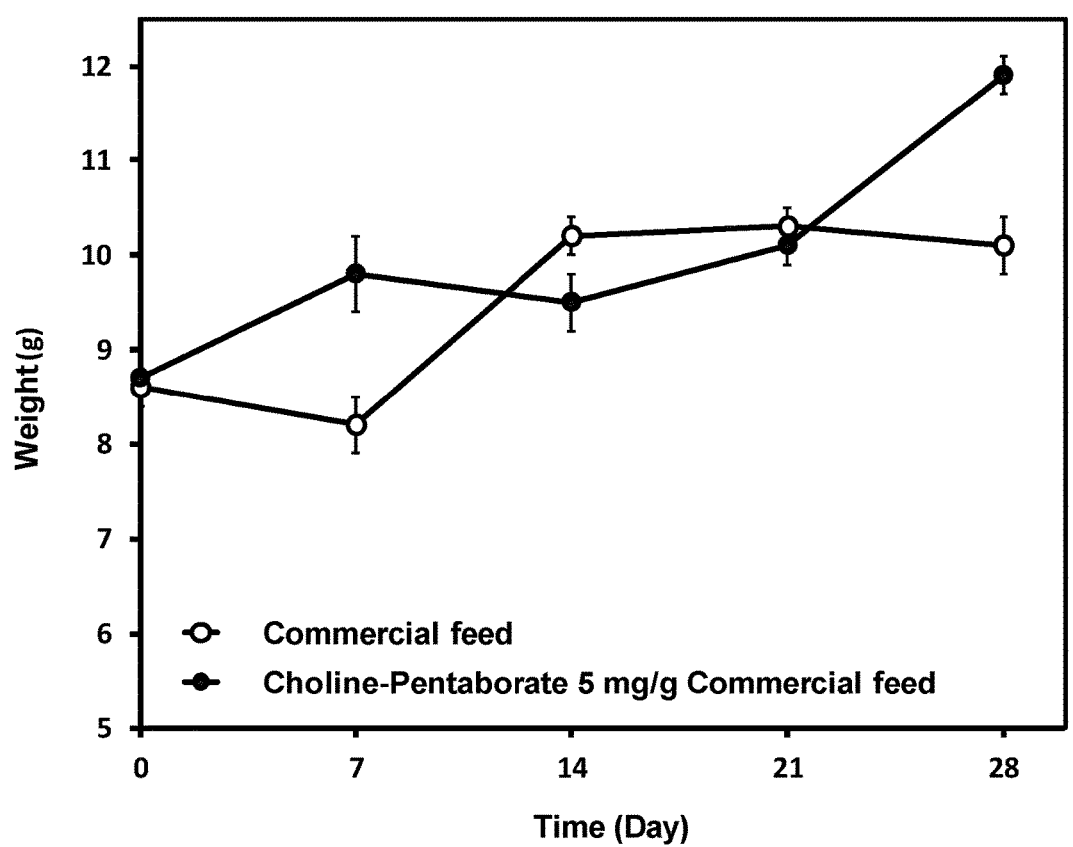
FIG. 6: Mean weight increase of shrimp over time fed a commercial diet and a commercial diet supplemented with choline/pentaborate complex. (*) Shrimp group fed with a commercial feed (control group); (Δ) Shrimp group fed with the commercial feed but supplemented with 5 mg of the choline/pentaborate complex/g. Both shrimp groups are fed daily ad libitum for to 28 days.

It is of interest to mention that the shrimp fed with the commercial diet supplemented 5 mg of choline/pentaborate complex had a 20% increment in mean weight, when compared with the shrimps control group (FIG. 6). After 14 days of treatment, shrimps are sampled for the DNA microarray analysis, but also to confirm that these shrimps are more resistant against WSSV and *V. parahaemolyticus* infections as previously reported.

7-6-2—DNA Microarray Analysis of Shrimp Treated with Choline/Pentaborate Complex The shrimp DNA microarray contains 60000 spots. Table 2 summarizes the classification of differential gene expression based in the patterns of absorbance source in two channels: Alexa-555 and Alexa-647 dye, and the number of Up- and Down-regulated genes in the microarray analysis.

Figure 7:
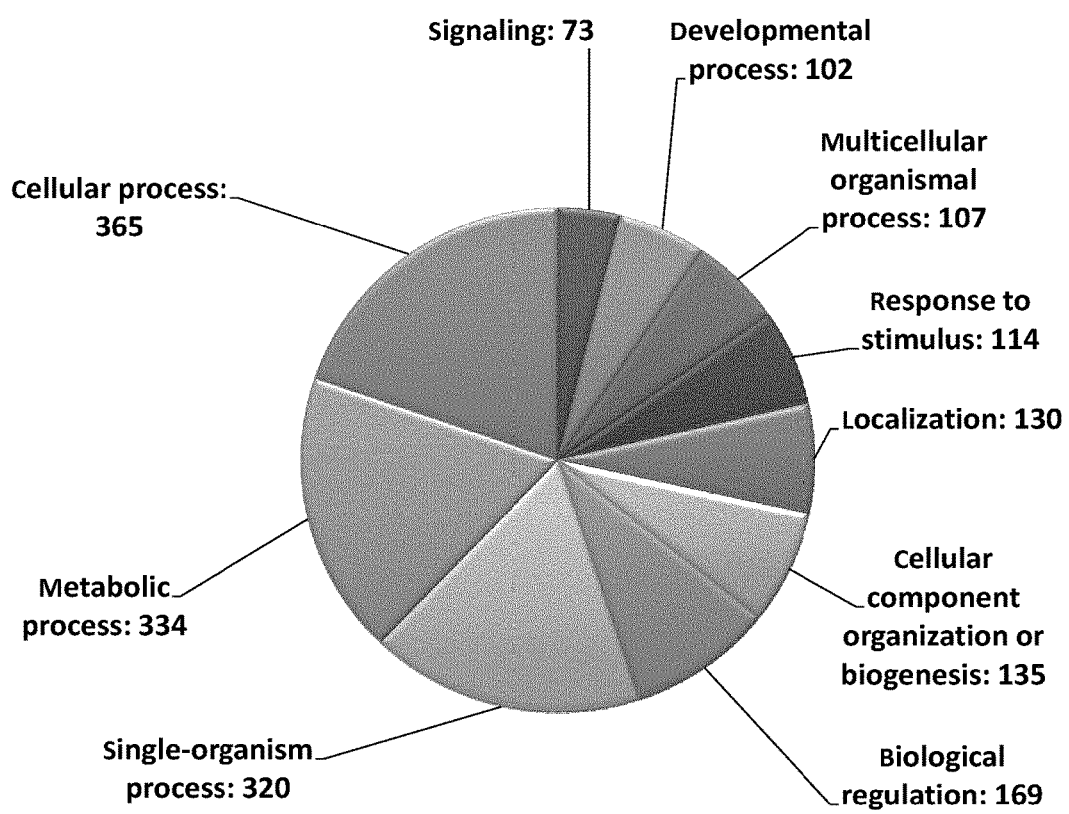
FIG. 7: Microarray functional annotation of 2 Up-regulated genes from microarray of the biological processes. The score is calculated for every node in the graph and sum of the distances to the GO original terms.

Down-regulated differentially expressed genes are submitted to Blast2GO suite for the assignment of several functional groups based on GO terminology. There were 583 Up-regulated genes in samples from shrimp fed for 14 days with the feed supplemented with choline/pentaborate complex at dose 5 mg/g, expressed genes fall into the followed biological processes:

1. Cellular Processes (20%);
2. Metabolic Process (18%);
3. Single-organism Process (17%);
4. Biological Regulation (9%);
5. Cellular Component Organization or Biogenesis (7%);
6. Localization (7%);
7. Response to Stimulus (6%);
8. Multicellular Organismal Process (6%);
9. Developmental Process (6%) and Signaling (4%) (FIG. 7).

The Molecular Functions of the 583 for 2-fold Up-regulated expressed genes fall into four categories:

10. Binding Activity (44%);

TABLE 1

Primer sequences used in the RT-qPCR

| NCBI Accession | Primer ID | Gene Name | Align Temp (° C.) | Sequence (5'-3') | Melt Peak (° C.) | Size (bp) |
|---|---|---|---|---|---|---|
| AY955373.1 | LvFerritinF LvFerritinR | Ferritin | 58 | CAAGCGAACCTCTGGAAATC TGGCAAATCCAGGTA GAGC | 83.5 | 230 |
| FE147224.1 | LvTollF LvTollR | Toll-like Receptor | 62 | GCCCTAAATGATGGATGAC GCCAAGGGAAAAAGAAAT | 88.2 | 151 |
| GU136229.1 | LvEF1AF LvEF1AR | Elongation Factor 1-α | 56 | CCA CACTGCTCACATTGC GAAGGTCTCCACGCACAT | 85.5 | 151 |
| JF288784.1 | LvACTBF LvACTBR | β-actin | 60 | TGGGACGACATGGAGAAG GGGGGTGTTGAAGGTCTC | 86.7 | 150 |
| X77318.1 | LvPAMYF LvPAMYR | Pre-amylase 1 | 58 | CCGTCTCCTATAAACTCGTCACTC TCGCCGTAGTTTTCAATGTTC | 88.5 | 259 |
| JQ277721.1 | LvTryF LvTryR | Trypsinogen 1 | 58 | TCGTCGGAGGAACTGACG TGCCCTCATCCACATCCT | 89.2 | 210 |
| FJ619564.1 | LvLIPF LvLIPF | Lipase Digestive 1 | PENDING | TCCTGGCTCACACACCTG GTCCTTCAGCGAGCCTTG | PENDING | 231 |
| X99730.1 | LvCPLF LvCPLR | Cathepsin L | PENDING | CGTCCTTCCAGTTCTACCAT ATCTGGATGTAGCCCTTGTT | PENDING | 166 |

TABLE 2

Statistical analysis of the number of Up- and Down-regulated genes in the DNA shrimp microarray analysis

| Expression Levels (Score) | Number of spots |
|---|---|
| All Spots | 60,000 |
| Spots available to analysis | 57,193 |
| Without signal | 37 |
| >2 | 1,650 |
| 1.5 to 2 | 1,984 |
| 1 to 1.5 | 3,662 |
| No regulated genes (−1 to 1) | 43,950 |
| −1.5 to −1 | 3,221 |
| −1.5 to −2 | 1,259 |
| <−2 | 1,434 |

7-6-3—Gene Ontology Analysis

Gene ontology (GO) is commonly used to categorize gene products and standardize their representation across species. In order to eliminate redundancy only the 2-fold Up- and Down-regulated differentially expressed genes are submitted to Blast2GO suite for the assignment of several functional groups based on GO terminology.

Figure 8:
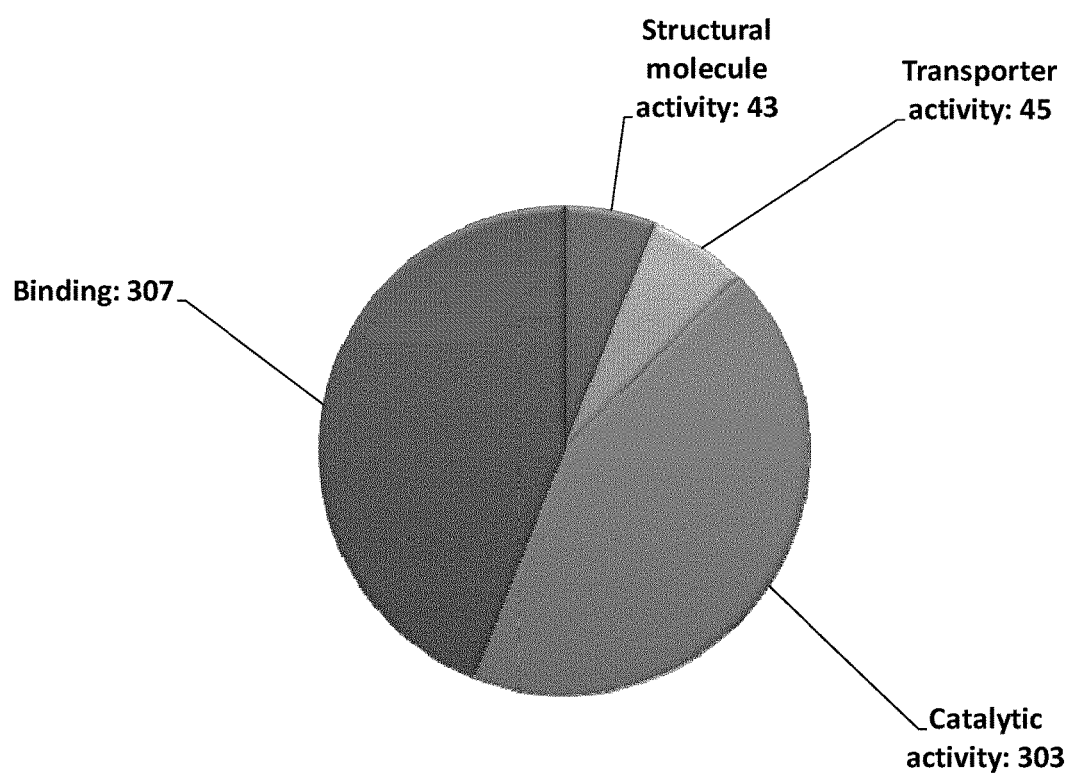
FIG. 8: Functional Annotation of 2 Up-regulated genes from microarray of the molecular function. The score is calculated for every node in the graph and sum of the distances to the GO original terms.

11. Catalytic Activity (43%);
12. Transporter Activity (7%);
13. Structural Molecule Activity (6%) (FIG. 8).

Figure 9:
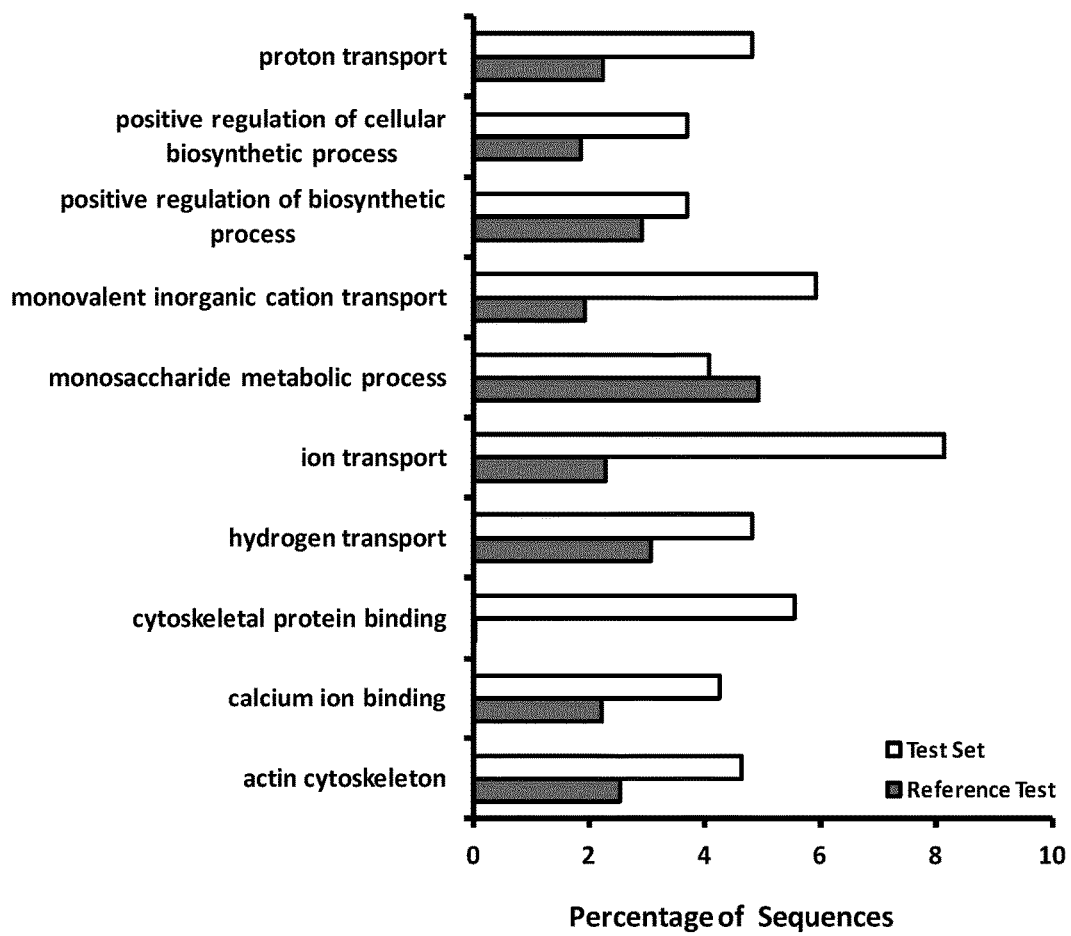
FIG. 9: Fischer Exact Test 2 Up-regulated GO terms versus all genes of GO Terms from microarray using α=0.01

The Fisher's exact test from GO terms of the 2-fold Up-regulated genes (shrimps treated with choline/pentaborate complex) versus all genes (shrimp control group) from DNA microarray shows that choline/pentaborate complex treated shrimps have gene with increased expression in the categories described as follows:

14. Ion Transport (8.15%);
15. Monovalent Inorganic Cation Transport (5.92%);
16. Cytoskeletal Protein Binding (5.55%);
17. Hydrogen Transport (4.81%);
18. Proton Transport (4.81%);
19. Actin Cytoskeleton (4.62%);
20. Calcium Ion Binding (4.25%);
21. Monosaccharide Metabolic Process (4.10%);
22. Positive Regulation of Biosynthetic Process (3.70%);
23. Positive Regulation of Cellular Biosynthetic Process (3.70%) (FIG. 9).

Figure 10:
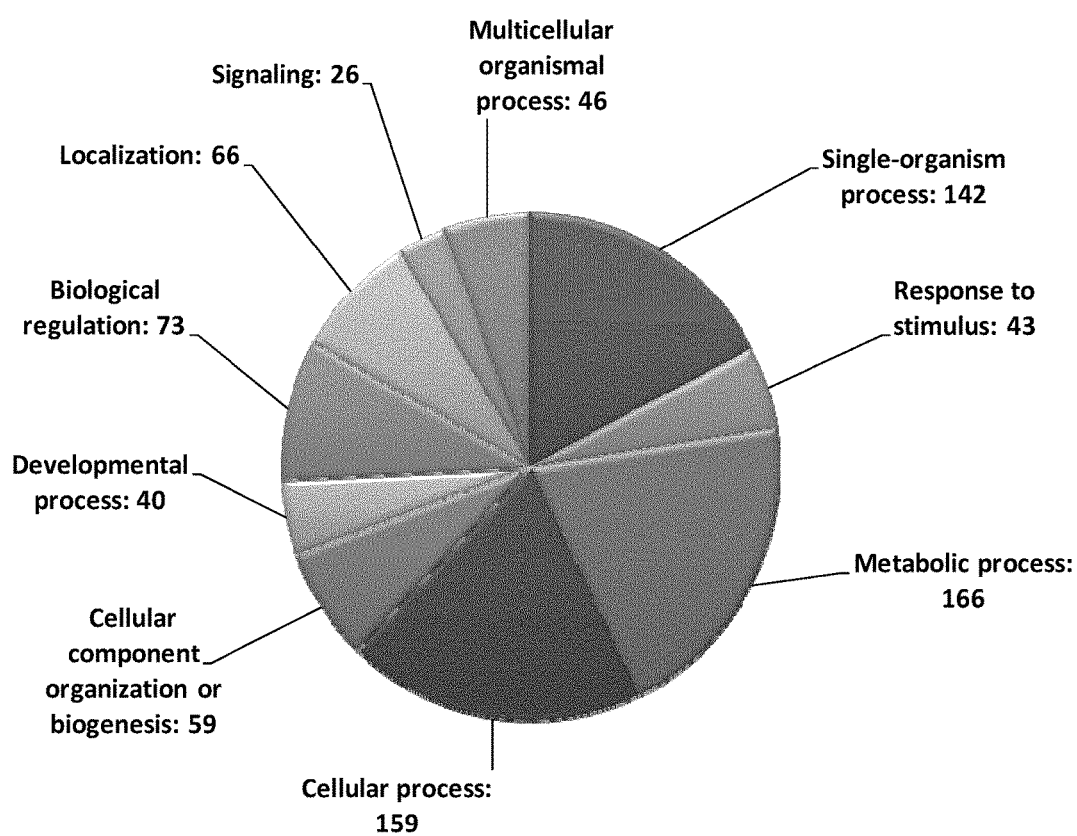
FIG. 10: Functional Annotation of 2 Down-regulated genes from microarray of the biological processes. The score is calculated for every node in the graph and sum of the distances to the GO original terms.

Regarding the Functional Annotation of the 2-fold Down-regulated expressed genes from the DNA microarray of the Biological Processes, it is found that there were 262 genes with a 2-fold Down-regulated expression in shrimp fed for 14 days with the feed supplemented with choline/pentaborate complex 5 mg/g, expressed genes fall into the followed Biological Processes:

24. Cellular Process (20%);
25. Metabolic Process (20%);
26. Response to Stimulus (5%);
27. Single-organism Process (17%);
28. Multicellular Process (6%);
29. Signaling (3%);
30. Localization (8%);
31. Biological Regulation (9%);
32. Developmental Process (5%);
33. Cellular Component Organization or Biogenesis (7%) (FIG. 10).

Figure 11:
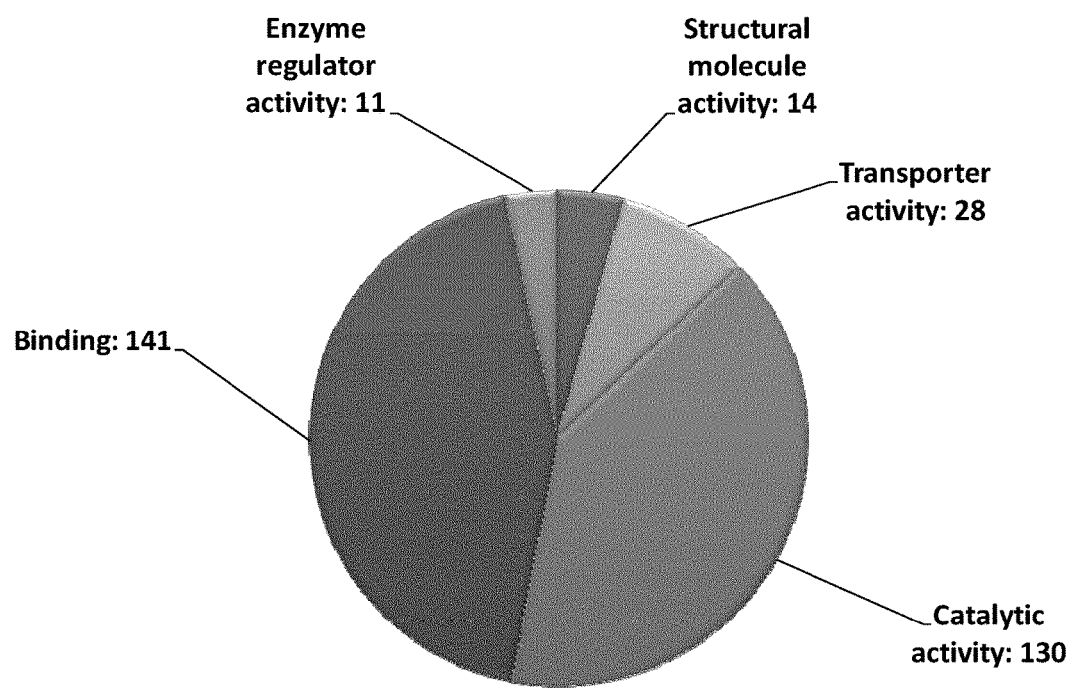
FIG. 11: Functional Annotation of 2 Down-regulated genes from microarray of the molecular function. The score is calculated for every node in the graph and sum of the distances to the GO original terms.

The Molecular Function of the 262 genes in the 2-fold Down-regulated expressed genes fall into four categories:

34. Binding (44%);
35. Catalytic Activity (40%);
36. Transporter Activity (9%);
37. Structural Molecule Activity (4%);
38. Enzyme Regulator Activity (3%) (FIG. 11).

Figure 12:
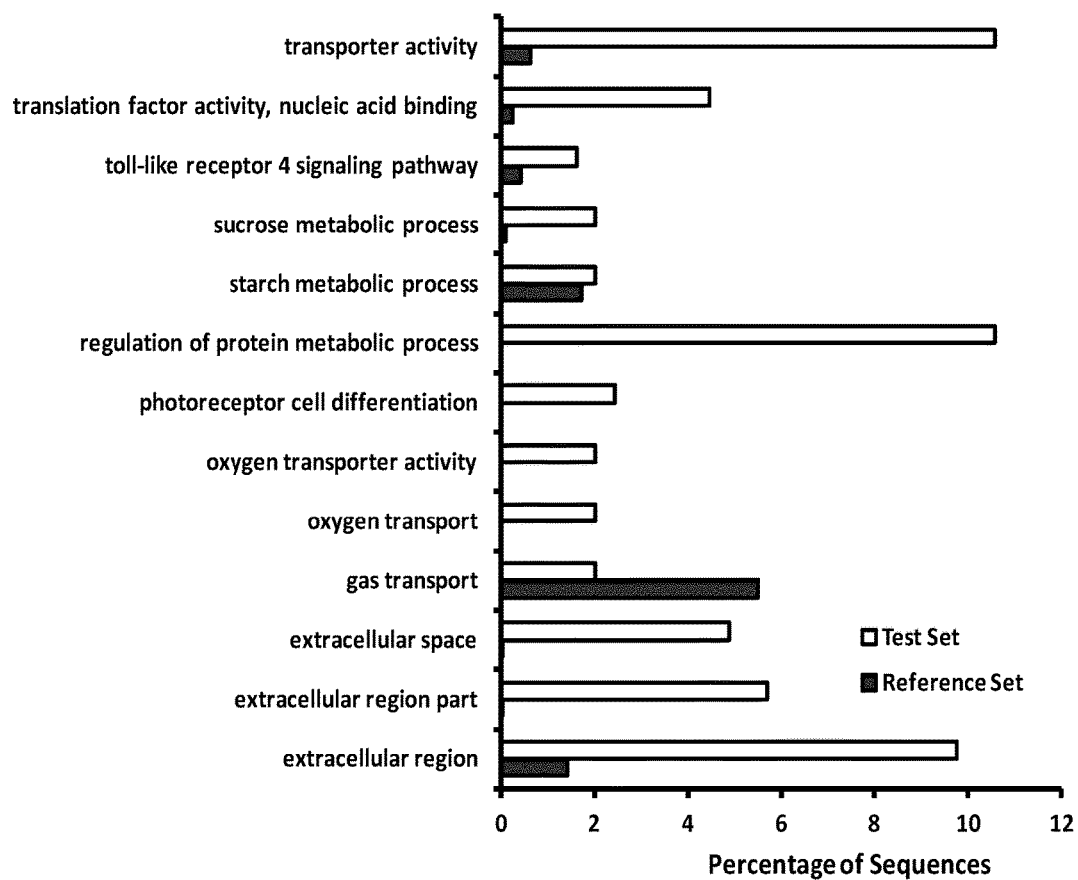
FIG. 12: Fischer Exact Test 2 Down-regulated GO terms versus all genes of GO Terms from microarray using α=0.01.

The Fisher's exact test from GO terms of the 2-fold Down-regulated genes (shrimps treated with choline/pentaborate complex) versus all genes (shrimp control group) from DNA microarray showed that shrimp treated with choline/pentaborate complex over-represented gene categories described as follows:

1. Regulation of protein metabolic process (10.56%);
2. Transporter activity (10.56%), extracellular region (9.75%);
3. Extracellular region part (5.69%), extracellular space (4.87%);
4. Translation factor activity, nucleic acid binding (4.47%);
5. Photoreceptor cell differentiation (2.43%);
6. Gas transport (2.03%);
7. Oxygen transporter activity (2.03%);
8. Starch metabolic process (2.03%);
9. Sucrose metabolic process (2.03%);
10. Toll-like Receptor for signaling pathway (1.62%) (FIG. 12).

7-6-4—Comparative Analysis of Metabolic Pathways

The *L. vannamei* transcriptomic sequences from the shrimp DNA microarray are compared to ESTs and nucleotide sequences from *Drosophila* present in the NCBI database in order to detect the presence of proteins that are over-expressed in different Metabolic Pathways. The results of the 2-fold Up-regulated genes, related to genes and enzyme expressed into each group are summarized in Table 3. Similarly, the results of the 2-fold Down-regulated genes, related to genes and enzyme expressed into each group are summarized in Table 4.

TABLE 3

Metabolic pathways of DNA shrimp microarray analysis of the 2-Up regulated genes in *L. vannamei* treated with the choline/pentaborate complex supplemented (5 mg/g) commercial feed.

| Metabolic Pathway | # Genes | # Enzymes |
|---|---|---|
| Oxidative phosphorylation | 18 | 5 |
| Purine metabolism | 14 | 7 |
| Glycolysis | 8 | 8 |

TABLE 3-continued

Metabolic pathways of DNA shrimp microarray analysis of the 2-Up regulated genes in *L. vannamei* treated with the choline/pentaborate complex supplemented (5 mg/g) commercial feed.

| Metabolic Pathway | # Genes | # Enzymes |
|---|---|---|
| Amino sugar and nucleotide Sugar metabolism | 8 | 7 |
| Glutathione metabolism | 7 | 5 |
| Pyruvate metabolism | 6 | 6 |
| Valine, leucine and isoleucine degradation | 6 | 6 |
| Cytochrome P450 | 6 | 3 |
| Pentose phosphate pathway | 5 | 4 |

TABLE 4

Metabolic pathways of DNA shrimp microarray analysis of the 2-Down regulated genes in *L. vannamei* treated with the choline/pentaborate supplemented (5 mg/g) commercial feed

| Metabolic Pathway | # Genes | # Enzymes |
|---|---|---|
| Oxidative phosphorylation | 6 | 4 |
| Pentose phosphate pathway | 5 | 5 |
| Starch and sucrose metabolism | 5 | 2 |
| Purine metabolism | 4 | 3 |
| Phenylpropanoid biosynthesis | 3 | 1 |
| Aminoacyl-tRNA biosynthesis | 3 | 3 |
| Glycolysis/Gluconeogenesis | 3 | 3 |
| Pentose and glucuronate interconversions | 3 | 2 |
| Phenylalanine metabolism | 3 | 1 |
| Ascorbate and aldarate metabolism | 3 | 2 |

7-6-5—Data Mining of the Immune Related Genes

A search of the DNA microarray analysis, with GO term: 0006955 (immune response), revealed the presence of an elevated number of relevant molecules for the immune response that are over-expressed after shrimp are fed for 14 days with the feed supplemented with choline/pentaborate complex 5 mg/g. The main components related to immune response in *L. vannamei* that are 2-fold Up-regulated are described in Table 5.

7-6-6—Validation of Specific Genes by RT-qPCR

Figure 13:
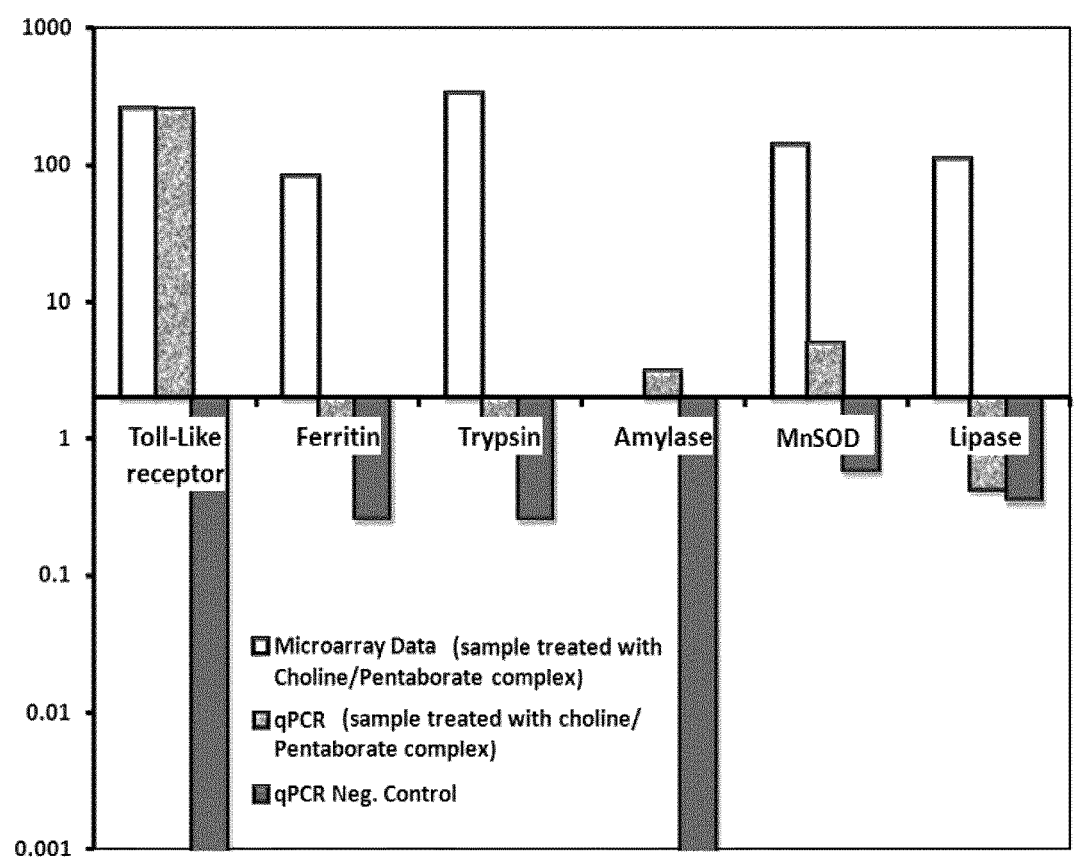
FIG. 13: RT q-PCR analysis of selected genes related to immune and digestive proteins of the shrimp, used to validate the DNA microarray assays.

Selected genes related to immune and digestive proteins presented in the shrimp DNA microarray (Table 1) are further validated by RT q-PCR, and the results are illustrated in the FIG. 13.

TABLE 5

Data mining of immune related genes from the 2 Up-regulated in the shrimp DNA Microarray

| # | NCBIID | Protein Description |
|---|---|---|
| 1 | 40958211 | Interleukin Enhancer Binding Factor |
| 2 | 52863030 | Probable Protein Brick1-like |
| 3 | 171595417 | Actin-related Protein 3 Isoform X2 |
| 4 | 171649044 | Protein Toll |
| 5 | 171484743 | Srsf Protein Kinase 2 |
| 6 | 171604948 | Profilin |
| 7 | 171640969 | Histone Acetyltransferase P300- Partial |
| 8 | 171533428 | Protein Red |
| 9 | 171638050 | Serine Threonine-protein Phosphatase 2a 65 Kda Regulatory SubunitA Alpha Isoform-like |
| 10 | 171601498 | Ubiquitin-40s Ribosomal Protein S27a |
| 11 | 171578425 | Ubiquitin Family Protein |
| 12 | 171527123 | Protein Lsm14 Homolog A Isoform X2 |
| 13 | 171576197 | Beta--Glucan-binding Protein |
| 14 | 171497789 | Sam Domain And Hd Domain-containing Protein 1 |
| 15 | 171616000 | Cathepsin C |

TABLE 5-continued

Data mining of immune related genes from the
2 Up-regulated in the shrimp DNA Microarray

| # | NCBIID | Protein Description |
|---|--------|---------------------|
| 16 | 171660130 | Glucosidase 2 Subunit Beta |
| 17 | 171644991 | Calmodulin |
| 18 | 171655889 | Cytoplasmic Partial |
| 19 | 171506897 | Dipeptidyl Peptidase 1 |
| 20 | 171534712 | Profilin |
| 21 | 171606038 | Dna-directed Rna Polymerases And Iii Subunit Rpabc5 |
| 22 | 171615285 | Dna-directed Rna Polymerase Iii Subunit Rpc6 |
| 23 | 171649584 | ExocystComplex Component2-like |
| 24 | 171524287 | Ubiquitin-40s Ribosomal Protein S27a |
| 25 | 171488738 | Ubiquitin-conjugating Enzyme E2 |
| 26 | 171580457 | Ubiquitin C |
| 27 | 171533219 | LrrAnd Pyd Domains-containing Protein 10 |
| 28 | 171626089 | A Chain Orally Active 2-amino Thienopyrimidine Inhibitors Of The Hsp90 Chaperone |
| 29 | 156637463 | LipopolysaccharideAnd Beta-glucan Binding Protein |
| 30 | 89258160 | Ecdysteroid-regulated Protein |
| 31 | 68271149 | Dead Box Helicase Partial |
| 32 | 1907112 | Bone Morphogenetic Protein 6 |
| 33 | 29838465 | Beta-glucan-binding Protein |

Globally, commercial shrimp diets supplemented with 5 mg choline/pentaborate complex by gram of feed are effective to stimulate the non-specific immune system of shrimp and to improve natural resistance of *L. vannamei* to WSSV and *Vibrio parahaemolyticus* infections.

Choline/pentaborate complex supplementation can increase the immunologic reactivity of shrimps as revealed by the number of immune related genes expressed in the DNA shrimp microarray analysis. There are at least 33 immune related genes that are over-expressed (Table 5). Some of these genes are further validated by RT q-PCR, and our results revealed that the expression of some of these genes, such as the Toll-Like Receptor and SOD increased more than 200 fold (FIG. 13), clearly indicating the immunostimulatory activity of choline/pentaborate complex supplementation of a commercial shrimp diet.

As arthropod species, shrimp mainly rely on the innate immune system, which consists of humoral and cellular responses against viral infections. The direct or indirect recognition of pathogens or pathogen-associated molecular patterns by germ line-encoded proteins called pattern recognition receptors (PRRs) that tightly related to Toll-like Receptors leads to rapid humoral and cellular immune responses (Li, F., Xiang, J. 2013. *Dev. Comp. Immunol.* 39, 11-26).

It is of interest to mention that invertebrates do not possess an adaptive immune system based on highly specific antibodies and antigen receptors. They must rely on efficient immune defense to protect them against invaders. It has been proven that hemocytes are key cells for innate invertebrate defense reactions. One important immune defense reaction of crustacean hemocytes is phagocytosis when the organism is attacked by microorganisms or viruses. During the course of phagocytosis, the host oxidases (e.g. NADPH oxidase, and particularly prophenol oxidase that is involved in the shrimp clotting system and in the innate immunity) get activated which in turn enhances the glycolytic reactions (explaining amylase gene over-expression) that will increase the consumption of oxygen, and induce the production of a mass of reactive oxygen species (ROS) such as superoxide anion ($O_2.^-$), hydrogen peroxide ($H_2O_2$) and hydroxyl radical (OH.). Though ROS can kill foreign invaders, the mass accumulation of these reactive molecules in animals can cause serious cell damage. WSSV infection can cause the release of ROS and increase the oxidative stress in shrimp and leads to a high level of lipid peroxidation. Consequently, the rapid elimination of these excessive ROS is essential for the proper functioning of cells and the survival of organisms. This is performed by antioxidant enzymes including superoxide dismutases (SOD) that scavenges the superoxide anions. SOD detoxifies superoxide radicals by converting them to hydrogen peroxide and oxygen. Hydrogen peroxide is then transformed to water and oxygen by catalase or other antioxidant compounds, providing innocuous compounds to the cell.

Besides over-expression of immune related genes in shrimp treated with diets supplemented with choline/pentaborate complex, other biological processes are modulated too in *L. vannamei*, including the expression of genes associated to: Response to stimuli (43), Metabolic process (166), Cellular process (159), Biogenesis (59), Developmental process (40), Biological regulation (73) Localization (66), and Signaling (26) (FIG. 10, Table 3).

Shrimp diets supplemented with choline/pentaborate complex at concentration of 5 mg/g of feed are effective in reducing the impact of WSSV infection when following standardized administration protocols. This represents a major breakthrough for the control of a disease that affects a significant number of commercial shrimp production operations. The inclusion of choline/pentaborate complex used as additive in commercial diets provides an efficient mechanism for stimulation of the shrimp immune system that contribute to improve natural resistance of *L. vannamei* to WSSV and *Vibrio parahaemolyticus* infections.

EXAMPLE-8

Other Quaternary Ammonium Compounds Used to Complex with Boric Acid or its Derivatives 8-1—Complexation of (2-Hydroxyethyl)Triethylammonium with Boric Acid (or its Derivatives)

Figure 14:
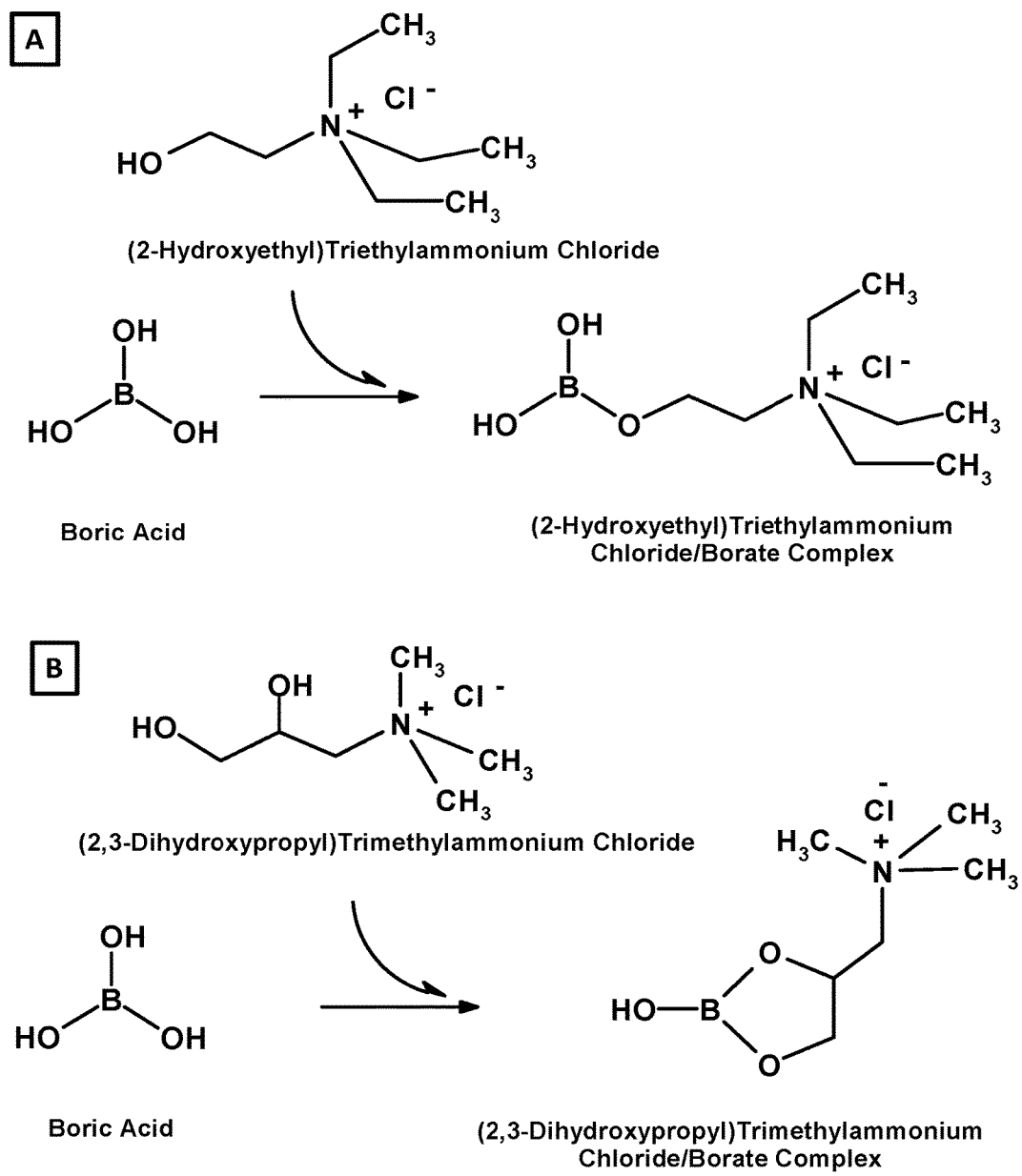
FIG. 14: illustrate the synthesis of complexes of other quaternary ammonium compounds with boric acid.

The complexation of (2-hydroxyethyl)triethylammonium and boric acid (or its derivatives) is prepared under identical conditions as described previously in EXAMPLE 1, except that (2-hydroxyethyl)triethylammonium is used, instead of (2-hydroxyethyl)trimethylammonium (FIG. 14-A)

8-2—Complexation of (2,3-Dihydroxyethyl)Triethylammonium with Boric Acid (or its Derivatives)

Since choline ([2-hydroxyethyl]trimethyl ammonium) possesses a hydroxyl group, the complexation could be less stable, because there is a hydroxyl groups involved in formation of the complex with boric acid (or its derivatives). Consequently, the use of choline having two hydroxyl groups such as (2,3-dihydroxypropyl)trimethylammonium chloride seems more stable probably due to its contribution of two hydroxyl groups in complexing with boric acid (or its derivatives).

The complexation of choline and boric acid is prepared under identical conditions as described previously in EXAMPLE 1, except that (2,3-dihydroxypropyl) trimethylammonium is used, instead of (2-hydroxyethyl)trimethylammonium (FIG. 14-B).

8-3—Complexation of Choline with Phenylboronic Acid

Figure 15:
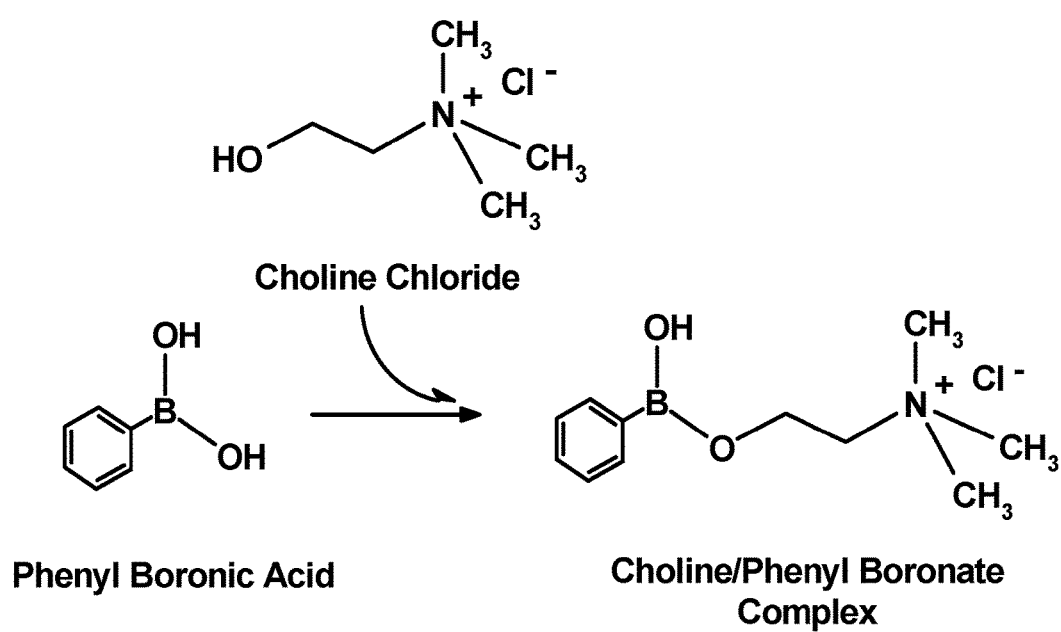
FIG. 15: illustrate the synthesis of choline/phenyl boronate complex.

The complexation of choline and phenylboronic acid is prepared under identical conditions as described previously in EXAMPLE 1, except that phenylboronic acid is used, instead of boric acid (FIG. 15) and the volume of distilled water is 800 mL, instead of 400 mL.

8-4—Complexation of Choline with Myristylboronic Acid

Figure 16:
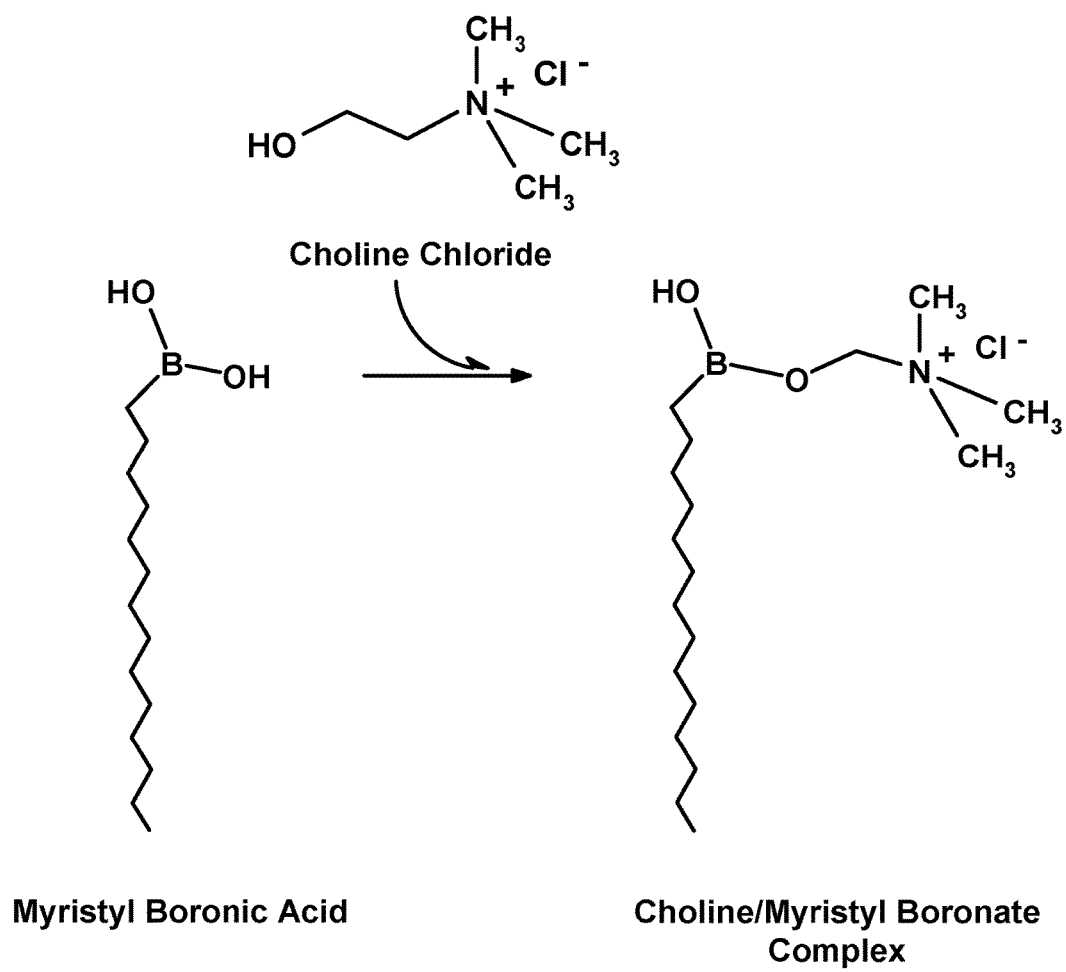
FIG. 16: illustrate the synthesis of choline/myristyl boronate complex.

The complexation of choline and phenylboronic acid is prepared under identical conditions as described previously for «Complexation of choline with phenylboronic acid», except that Myristylboronic acid is used, instead of phenylboronic acid (FIG. 16).

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A compound of formula I, or a pharmaceutically acceptable salts thereof, and stereoisomers thereof:

(I)

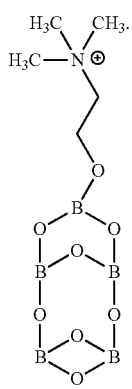

2. A combination of the compound of claim 1, with any one of the following compounds or a pharmaceutically acceptable salts thereof, and stereoisomers thereof:

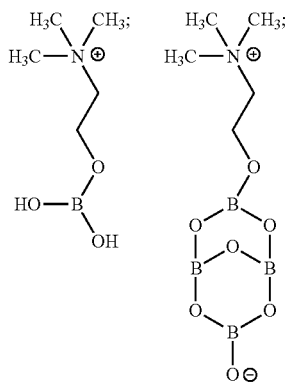

or a combination thereof.

3. A pharmaceutical composition comprising a compound of claim 1, or a pharmaceutically acceptable salt thereof, and a pharmaceutically acceptable carrier.

4. A composition comprising a compound of claim 1, or a pharmaceutically acceptable salt thereof, and an acceptable carrier.

5. The composition of claim 4, for use in the treatment or prevention of a pathogenic infection in a crustacean in need thereof.

6. The pharmaceutical composition of claim 3, further comprising any one of the following compounds or a pharmaceutically acceptable salts thereof, and stereoisomers thereof:

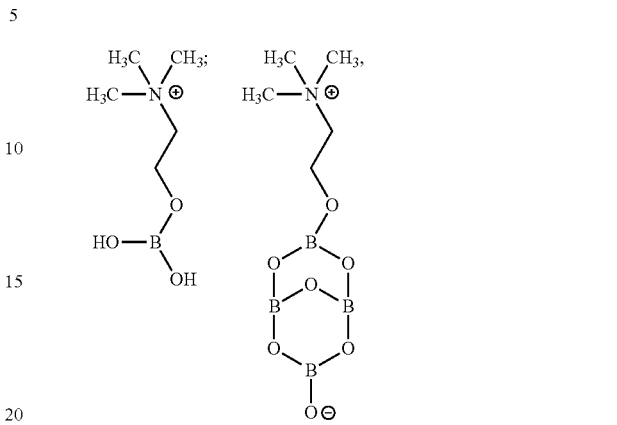

or a combination thereof.

7. The composition of claim 4, further comprising any one of the following compounds or a pharmaceutically acceptable salts thereof, and stereoisomers thereof:

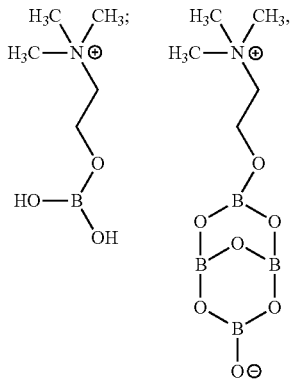

or a combination thereof.

8. The composition of claim 7, for use in the treatment or prevention of a pathogenic infection in a crustacean in need thereof.

* * * * *